(12) United States Patent
Golomb et al.

(10) Patent No.: US 8,178,128 B2
(45) Date of Patent: May 15, 2012

(54) NANOPARTICLES CONTAINING POLYMERIC NUCLEIC ACID HOMOLOGS

(75) Inventors: Gershon Golomb, Efrat (IL); Haigt Sacks, Jerusalem (IL); Yousef Najareh, Jerusalem (IL); Elia Fishbein, Jerusalem (IL); Michael Chorny, Jerusalem (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 798 days.

(21) Appl. No.: 10/497,783

(22) PCT Filed: Dec. 5, 2002

(86) PCT No.: PCT/IL02/00985
§ 371 (c)(1),
(2), (4) Date: Dec. 13, 2004

(87) PCT Pub. No.: WO03/048298
PCT Pub. Date: Jun. 12, 2003

(65) Prior Publication Data
US 2006/0051426 A1      Mar. 9, 2006

Related U.S. Application Data

(60) Provisional application No. 60/335,837, filed on Dec. 5, 2001.

(51) Int. Cl.
*A61K 9/16* (2006.01)
*C12N 15/11* (2006.01)

(52) U.S. Cl. .................................. 424/491; 514/44 A

(58) Field of Classification Search .......... 435/6, 91.31, 435/455, 458; 514/44, 44 A; 536/23.1, 24; 424/9.322, 491
See application file for complete search history.

(56) References Cited

U.S. PATENT DOCUMENTS

| | | | |
|---|---|---|---|
| 3,791,932 A | 2/1974 | Schuurs et al. | |
| 3,839,153 A | 10/1974 | Schuurs et al. | |
| 3,850,578 A | 11/1974 | McConnell | |
| 3,850,752 A | 11/1974 | Schuurs et al. | |
| 3,853,987 A | 12/1974 | Dreyer | |
| 3,867,517 A | 2/1975 | Ling | |
| 3,879,262 A | 4/1975 | Schuurs | |
| 3,901,654 A | 8/1975 | Gross | |
| 3,935,074 A | 1/1976 | Rubenstein | |
| 3,984,533 A | 10/1976 | Uzgiris | |
| 3,996,345 A | 12/1976 | Ullman | |
| 4,034,074 A | 7/1977 | Miles | |
| 4,036,945 A | 7/1977 | Haber | |
| 4,098,876 A | 7/1978 | Piasio | |
| 4,331,647 A | 5/1982 | Goldenberg | |
| 4,666,828 A | 5/1987 | Gusella | |
| 4,683,202 A | 7/1987 | Mullis | |
| 4,736,866 A | 4/1988 | Leder et al. | |
| 4,801,531 A | 1/1989 | Frossard | |
| 4,816,567 A | 3/1989 | Cabilly | |
| 4,866,042 A | 9/1989 | Neuwelt | |
| 4,879,219 A | 11/1989 | Wands | |
| 4,946,778 A | 8/1990 | Ladner | |
| 5,011,771 A | 4/1991 | Bellet | |
| 5,175,383 A | 12/1992 | Leder et al. | |
| 5,175,384 A | 12/1992 | Krimpenfort | |
| 5,175,385 A | 12/1992 | Wagner | |
| 5,192,659 A | 3/1993 | Simons | |
| 5,221,778 A | 6/1993 | Byrne | |
| 5,272,057 A | 12/1993 | Smulson | |
| 5,281,521 A | 1/1994 | Trojanowski | |
| 5,288,846 A | 2/1994 | Quertermous | |
| 5,298,422 A | 3/1994 | Schwartz | |
| 5,347,075 A | 9/1994 | Sorge | |
| 5,360,735 A | 11/1994 | Weinshank | |
| 5,387,742 A | 2/1995 | Cordell | |
| 5,464,764 A | 11/1995 | Capecchi | |
| 5,487,992 A | 1/1996 | Capecchi | |
| 5,545,806 A | 8/1996 | Lonberg | |
| 5,545,807 A | 8/1996 | Surani | |
| 5,569,825 A | 10/1996 | Lonberg | |
| 5,625,126 A | 4/1997 | Lonberg | |
| 5,633,425 A | 5/1997 | Lonberg | |
| 5,661,816 A | 8/1997 | Fantone | |
| 6,133,246 A * | 10/2000 | McKay et al. | .................. 514/44 |
| 6,207,195 B1 * | 3/2001 | Walsh et al. | .................. 424/489 |
| 6,248,720 B1 * | 6/2001 | Mathiowitz et al. | ............ 514/44 |
| 6,635,623 B1 * | 10/2003 | Hoogeveen et al. | ............ 514/44 |

FOREIGN PATENT DOCUMENTS

WO          WO93/14200          7/1993

(Continued)

OTHER PUBLICATIONS

Peracchi, A., et al., Rev. Med. Virol., vol. 14, pp. 47-64 (2004).*
Chirila, T., et al., Biomaterials, vol. 23, pp. 321-342 (2002).*
Agrawal, S., et al., Molecular Med. Today, vol. 6, pp. 72-81 (2000).*
Crooke, S.T., Annu. Rev. Med. , vol. 55, pp. 61-95 (2004).*
Opalinska, J.B., et al., Nature Rev., vol. 1, pp. 503-514 (2002).*
Branch, A., Trends in Biochem. Sci., vol. 23, pp. 45-50 (1998).*
Crooke, S., Ann. Rev. Medicine, vol. 55, pp. 61-95 (2004).*
Peracchi et al., Rev. Med. Virol., vol. 14, pp. 47-64 (2004).*
Agrawal et al., Molecular Med. Today, vol. 6, pp. 72-81 (2000).*
Chirila et al., Biomaterials, vol. 23, pp. 321-342 (2002).*
Opalinska et al., Nature Rev., vol. 1, pp. 503-514 (2002).*
Jang et al., Expert Rev. Medical Devices, vol. 1, No. 1, pp. 127-138 (2004).*
Mahato et al. (1999) Pharmacuetical Perspectives of Nonviral Gene Therapy Adv Genet 41: 95-156.
Ledley (1994) Non-viral Gene Therapy Curr Opin Biotechnol 5: 626-636.

(Continued)

*Primary Examiner* — J. E. Angell
(74) *Attorney, Agent, or Firm* — Dahna S. Pasternak; Robins & Pasternak LLP

(57) ABSTRACT

A nanoparticle capable of delivery of an encapsulated molecule into a living cell. The nanoparticle includes an encapsulation media and an isolated nucleic acid homolog sequence. The encapsulation media is primarily polymeric. The nanoparticles release the encapsulated molecule over an extended period of time. Further disclosed are pharmaceutical compositions and articles of manufacture including nanoparticles and methods of preparing and using the nanoparticles.

5 Claims, 18 Drawing Sheets

FOREIGN PATENT DOCUMENTS

| | | |
|---|---|---|
| WO | WO94/06908 | 3/1994 |
| WO | WO94/23049 | 10/1994 |
| WO | WO94/28123 | 12/1994 |
| WO | WO 98/51812 | * 11/1998 |
| WO | WO 99/36090 | * 7/1999 |

OTHER PUBLICATIONS

Ledley (1995) Nonviral Gene Therapy the promise of Genes as Pharmacuetical Products Hum Gene Ther 6: 1129-1144.
Roy et al. (1999) Oral Gene delivery with chitosan DNA nanoparticles generates immunologic protection in a murine model of peanut allergy Nature Med 5: 387-391.
Chonn & Cullis (1998) Recent advances in lipsome technologies and their applications for systemic gene delivery AdvDrug Del Rev 30: 73-83.
Bonadio et al. (1998) Gene Therapy for tissue repair and regeneration Adv Drug Del Rev 33: 53-69.
Labhasetwar et al. (1998) A DNA controlled release coating for gene transfer; Transfection in Skeletal and Cardiac Muscle—JPharm Sci 1998; 87: 1347-1350.
Shea et al (1999) DNA delivery from polymer matrices for tissue engineering Nat Biotechnol 17: 551-554.
Smith et al. (1997) Toward Development of a Non-Viral Gene Therapeutic Adv Drug Del Rev 26: 135-150.
Mathiowitz et al. (1997)Biologically erodable rnicrospheres as potentional oral drug delivery systems Nature 386: 410-414.
Hedley et al. (1998), Microspheres containing plasmid-encoded antigens elicit cytotoxic T-cell responses Nature Med 4: 365-368.
Leong et al. (1998) DNA polyeation nanospheres as non-viral gene delivery vehicles J Control Rel 53: 183-193.
Labhasetwar et al1999) Gene transfection using biodegradable nanospheres : results in tissue culture and a rat osteotomy model Colloids and Surfaces B:Biointerfaces 16: 281-290.
Ledley (1996) Pharmaceutical approach to Somatic Gene Therapy—Pharm Res 13: 1595-1614.
Jong et al. (1997)Controlled release of plasmid DNA J Control Rel 1997; 47: 123-134.
Luo et al. (1999) Controlled DNA Delivery Systems—Pharm Res 16:1300-1308.
Ando et al. (1999) PLGA Microspheres containing plasmid DNA Preservation of supercoiled DNA via Cryopreparation and Carbohydrate Stablilization J Pharm Sci 88: 126-130.
Stein (2001) The experimental use of antisense oligonucleotides : a guide for the perplexed J. Clin. Invest. 108:641-4.
Akhtar et al. (1992)Cellular uptake and intracellular fate of antisense oligonucleotides Trends Cell Biol. 2:139-144.
Mahato et al. (1997) Development of targeted delivery systems for nucleic acid drugs *J. Drug Target.* 4:337-357.
Romano et al. (2000) Latest developments in gene transfer achievements perspectives and controversies over therapeutic applications *Stem Cells.* 18:19-39.
Romano et al. (1999) Gene transfer technology in therapy current application and future goals *Stem Cells.* 17:191-202.
Dani (1999) The challenge of vector development in gene therapy *Braz. J. Med Biol. Res.* 32:133-145.
Li et al. (2000) Nonviral gene therapy: promises and challenges *Gene Ther.* 7:31-34.
Lambert et al. (2001) Nanoparticulate systems for the delivery of antisense oligonucleotides *Adv. Drug. Del. Rev.* 47(1):99-112 Fig. 2.
Ray &Norden (2000)Peptide nucleic acid (PNA) its medical and biotechnical applications and promise for the future, *FASEB J.* 14:1041-60.
Soomets et al. (1999) Antisense properties of peptide nucleic acids *Front. Biosci.* 1:4D782-6.
Doyle DF et al. (2001) Inhibition of gene expression inside cells by peptide Nucliec acids Effect of mRNA target Sequence mismatched bases and PNA length *Biochemistiy*.40:53-64.
Dean (2000) Peptide nucleic acids : versatile tools for gene therapy strategies *Adv. Drug Del. Rev.* 44:81-95.
Fishbein et al. (2000) Local Delivery of platelet Derived Growth Factor receptor—Specific tyrphostin. Inhibits Neointimal formation in Rats. *Arterioseler Thromb Vasc Biol.* 20:667-76.

Fishbein et al. (2000)Nanoparticulate delivery system of a tyrphostin for the treatment of restenosis *J. Controlled Release.* 65:221-9.
Hughes et al. (1996) Platelet Derived Growth Factor (PDGF) Actions and Mechanisms in Vascular Smooth Muscle *Gen. Pharmac.* 27:1079-1089.
Noiseux et al. (2000) Bolus Endovasculat-PDGFRβ Antisense Treatment Suppressed Intimal Hyperplasia in a Rat Carotid Injury Model *Circ.* 102:1330-1336.
Sirois et al. (1997) Antisense Oligonucleotide Inhibition of PDGFR-β Receptor Subunoit Expression Directs Supression of Intimal Thickening *Circulation.* 95:669-676.
Villa et al. (1995) effects of Antisense c-myb Oligonucleotides on Vascular Smooth Muscle Cell Proliferation and Response to Vessel Wall Injury *Circ. Res.* 76:505-513.
Porter, R. R., The Hydrolysis of Rabbit γ Globulin and Antibodies with Crystalline Papain Biochem. J., 73: 119-126, 1959.
Inbar et al., Localization of Antibody-Combining Sites Within The Variable Portions of Heavy and Light Chains Proc. Nat'l Acad. Sci. USA 69:2659-62, 1972.
Whitlow and Filpula,—Single chain Fv Proteins and their fusion proteins Methods a companion to methods in Enzymology vol. 2, 2: 97-105, 1991.
Bird et al., Single Chain Antigen Binding proteins Science 242:423-426, 1988.
Pack et al., Improved Bivalent Miniantibodies with Identical Avidity as whole Antibodies Produced by High Cell Density Fermentation of *Escherichia coli* Bio/Technology 11:1271-77, 1993.
Larrick and Fry, PCR Amplification of Antibody Genes Methods, 2: 106-10, 1991.
Presta, Antibody engineering Curr. Op. Struct. Biol., 2:593-596 (1992)].
Jones et al., Replacing the complementarity determining regions in a human antibody with those from a mouse Nature, 321:522-525 (1986).
Riechmann et al., Reshaping Human Antibodies for Therapy, Nature 332:323-327 (1988).
Verhoeyen et al., Reshaping Human Antibodies : Grafting an Antilysozyme Activity—Science, 239:1534-1536 (1988).
Hoogenboom and Winter, By-passing Immunisation Human Antibodies from Synthetic Repertoires of Germline Vh Gene Segments Rearranged in Vitro . Mol. Biol., 227:381 (1991).
Marks et al., By-passing Immunisation Human Antibodies from V-gene Libraries Displayed on Phage J. Mol. Biol., 222:581 (1991)].
Boemer et al., Production of Antigen Specific Human Monoclonal Antibodies From In Vitro-Primed Human Splenocytes J. Immunol., 147(1):86-95 (1991).
Marks et al., By Passing Immunization: Building High Affinity Human Antibodies by Chain Shuffling Bio/Technology 10, 779-783 (1992).
Lonberg et al., Antigen specific human antibodies from mice comprising four distinct genetic modifications Nature 368 856-859 (1994).
Morrison, Success in specification Nature 368 812-13 (1994).
Fishwild et al., High—avidity human IgGk monoclonal antibodies from a novel strain of minilocus transgenic mice Nature Biotechnology 14, 845-51 (1996).
Neuberger,Generating high-avidity human Mabs in mice—Nature Biotechnology 14, 826 (1996).
Welch et al., "Expression of ribozymes in gene transfer systems to modulate target RNA levels." Curr Opin Biotechnol. Oct. 1998;9(5):486-96.
Welch et al., "Ribozyme gene therapy for hepatitis C virus infection." Clin Diagn Virol. Jul. 15, 1998;10(2-3):163-71.
Matveeva et al. (1998) Prediction of antisense oligonucleotide efficacy by in vitro methods *Nature Biotechnology* 16, 1374-1375.
Walton et al. (1999) Prediction of Antisense Oligonucleotide Binding Affinity to a Structured RNA target Biotechnol Bioeng 65(1):1-9.
Ray & Norden (2000) Peptide nucleic Acid (PNA) its medical and biotechnical applications and promise for the future *FASEB J.* 14:1041-60.
Remington's Pharmaceutical Sciences, 18th Ed., 1990, ISBN#: 0192734027, Mack pub Co.

Fingl, et al., 1975, in "The Pharmacological Basis of Therapeutics", Ch. 1 p. 1.

Sambrook et al., (1989) Molecular Cloning: A laboratory Manual.

Selected Methods in Cellular Immunology, W. H. Freeman and Co., New York (1980).

Transcription and Translation Hames, B. D., and Higgins S. J., eds. (1984).

PCR Protocols: A Guide to Methods and Applications, Academic Press, San Diego, CA (1990) Innis et al.

Slomkowski (1989) Synthesis of Low-Polydispersity (tetramethylene oxide) using Benzil and Pyrene Derivatives as Initiators *Macromolecules* 22: 503-509.

Hedin and Thyberg (1985) Receptor mediated endocytosis of immunogloblin-coated colloidal gold particles in cultured mouse periotoneal macrophages. Chloroquine and monensin inhibit transferof the ligand from endocytic vesicles to lysosomes *Eur J Cell Biol* 39: 130-135.

Kato et al. (1984) The effects of sucrose loading on lysosomal hydrolases *Mol Cell Biochem* 60:83-98.

Golomb et al. (1996) Controlled Delivery of a Tyrphostin Inhibits Intimal Hyperplasia In a Rat Carotid Artery Injury Model Atherosclerosis. 125:171-182.

Levy (1996) Characterization of plasmid DNA transfer into mouse skeletal muscle; evaluation of uptake mechanism expression and secretion of gene products into blood Gene Therapy 3: 201-211.

Burke and Olson, Preperation of clone libraries in Yeast Artificial Chromosome Vectors Methods in Enzymology, 194:251-270 1991.

Capecchi, Altering the Genome by Homologous Recombination Science 244:1288-1292 1989).

Davies et al., Targeted alterations in yeast artificial chromosomes for inter-species gene transfer Nucleic Acids Research, 20 (11) 2693-2698 1992).

Dickinson et al., High Frequency Gene Targeting Using Insertional Vectors—Human Molecular Genetics, 2( 8): 1299-1302 (1993).

Huxley et al., The Human HPRT Gene on a Yeast Political Chromosome Is functional when transferred to Mouse cells by cell fusion Genomics, 9:742-750 1991).

Jakobovits et al., Germ-line transmission and expression of a human-derived yeast artificial chromosome Nature, 362:255-261 1993).

Lamb et al., Introduction and expression of the 400 kilobase *precursor amyloid protein* gene in transgenic mice Nature Genetics, 5: 22-29 1993.

Pearson and Choi, Expression of the human β-amyloid precursor protein gene from a yeast artificial chromosome in transgenic mice Proc. Natl. Acad. Sci. USA 1993). 90:10578-82.

Rothstein, Targeting Disruption replacement and allele rescue integrative DNA transformation in Yeast Methods in Enzymology, 194:281-301 1991).

Schedl et al., A yeast artificial chromosome covering the tryosinase gene confers copy number dependant expression in transgenic mice Nature, 362: 258-261 1993).

Strauss et al.,Germ Line transmission of a yeast artificial chromosome spanning the murine α 1 Science, 259:1904-1907 1993) Gene Therapy (Advances in Pharmacology 40, Academic Press, (1997).

Chang et al., Somatic Gene Therapy, CRC Press, Ann Arbor, MI 1995).

Oligocalculator, 3.02, supplied by Northwestern University, Chicago Illinois (http://www.basic.northwestern.edu/biotools/OligoCalc.html); described in "Kibba WA. 'OligoCalc: an online oligonucleotide properties calculator'. Nucleic Acids Research, 2007, vol. 35, No. suppl_2 W43-W46".

Rolland AP.(1998) From genes to gene medicines: recent advances in nonviral gene delivery. Crit Rev Ther Drug Carrier Syst. 1998;15(2):143-98.

Chorny et al. (2000) Drug delivery systems for the treatment of restenosis Crit Rev Ther Drug Carrier Syst. 2000;17(3):249-84.

S.P.C. Cole, D. Kozbor and J.C. Roder. The EBV-hybridoma technique and its application to human lung cancer. In, Monoclonal Antibodies and Cancer Therapy (vol. 27, UCLA Symposia on Molecular and Cellular Biology, New Series) (eds. R.A. Reisfeld and S.Sell), pp. 77-96, Alan R. Liss, Inc. N. Y., 1985.

Lonberg and Huszar, Intern. Rev. Immunol. 13 65-93 (1995). Int Rev Immunol. 1995;13(1):65-93. Human antibodies from transgenic mice.

Fishbein et al. pp. 313-335. In: Wise DL, ed. Biomaterials and bioengineering handbook. New York: Marcel Dekker, Inc; 2000 pp. 313-335.

Gilboa et al. (Biotechniques 4 (6): 504-512, 1986) Title: Transfer and Expression of Cloned Genes Using Retroviral Vectors Author(s): Gilboa E, Eglitis MA, Kantoff PW, Anderson WF Source: Biotechniques 4 (6): 504-512 Nov.-Dec. 1986.

Nielsen PE (2000) Antisense peptide nucleic acids. Curr Opin Mol Ther 2000; 2:282-7.

Weinstein R, Hoover GA, Stemerman MB, van der Spek J, Maciag T. Fibronectin dependence for attachment in vitro: smooth muscle versus fibroblast. In: Sato GH, Pardee AB, Sirbasku DA, eds. Growth of cells in hormonally defined media. Cold Spring Harbor: Cold Spring Harbor Laboratory; 1982:145-154.

Yamada KM, Kennedy DW, Hayashi M. Fibronectin in cell adhesion, differentiation, and growth. In: Sato GH, Pardee AB, Sirbasku DA, eds. Growth of cells in hormonally defined media. Cold Spring Harbor: Cold Spring Harbor Laboratory; 1982:131-143.

* cited by examiner

DNA  PT-ODN  PNA

FIGURE 2a
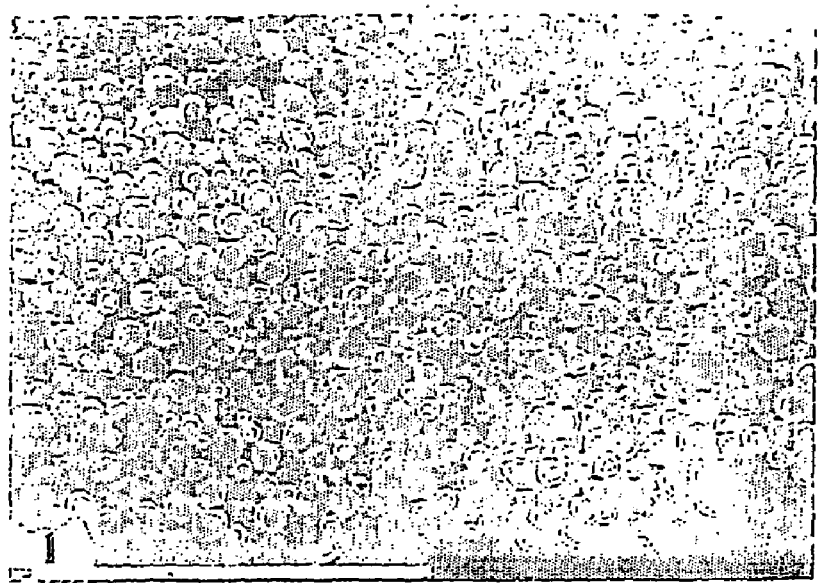
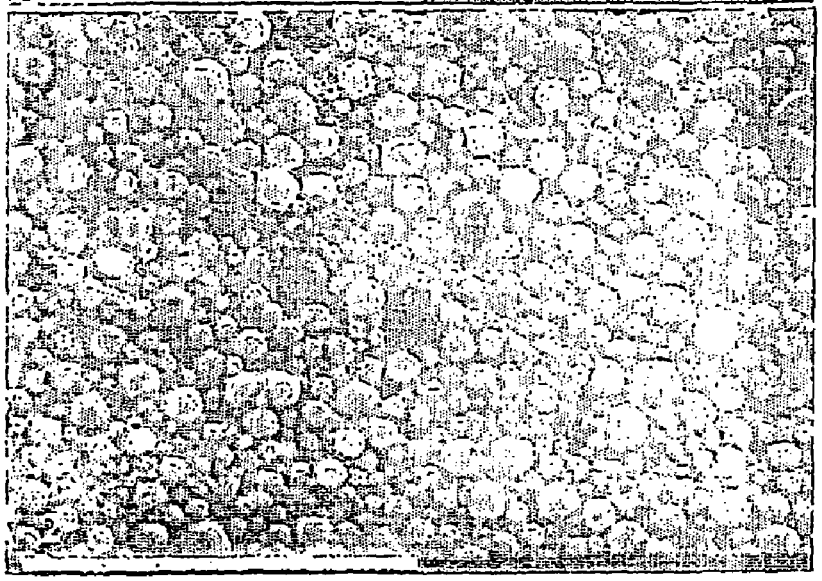
FIGURE 2b
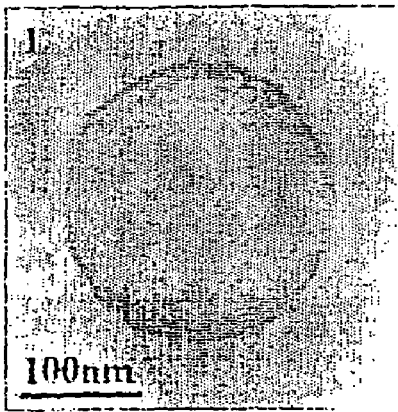
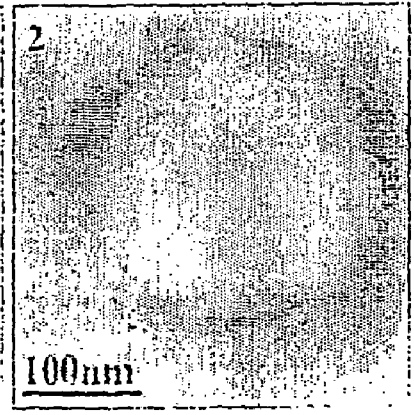

FIGURE 3
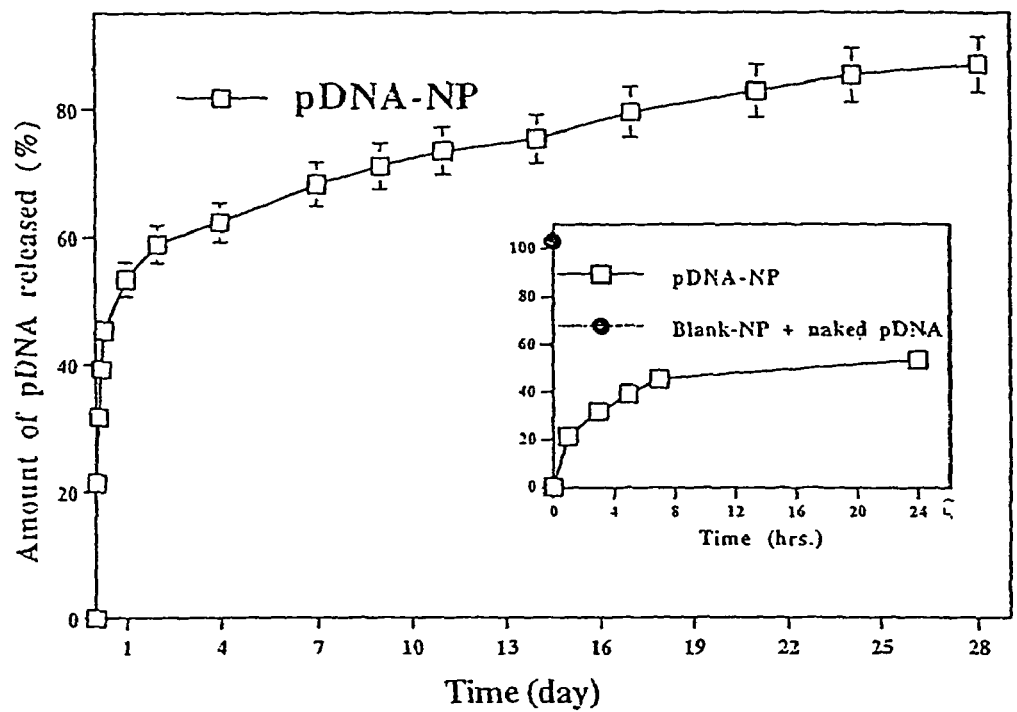
Figure 4a
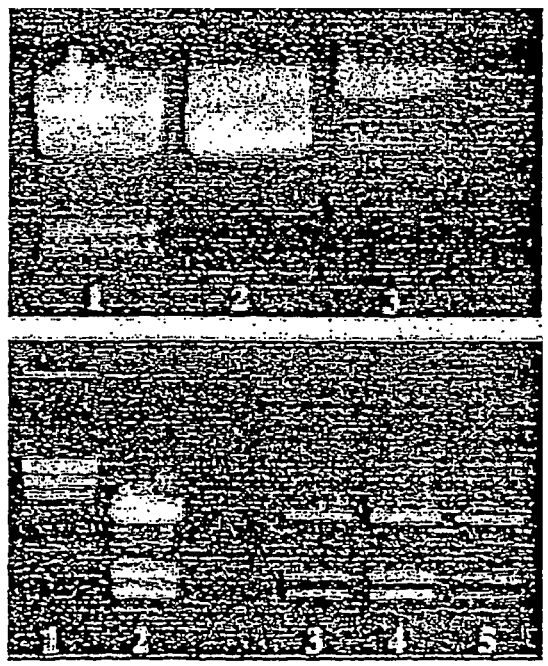
Figure 4b

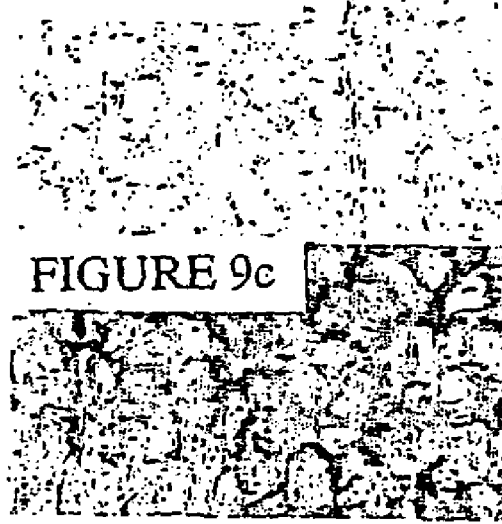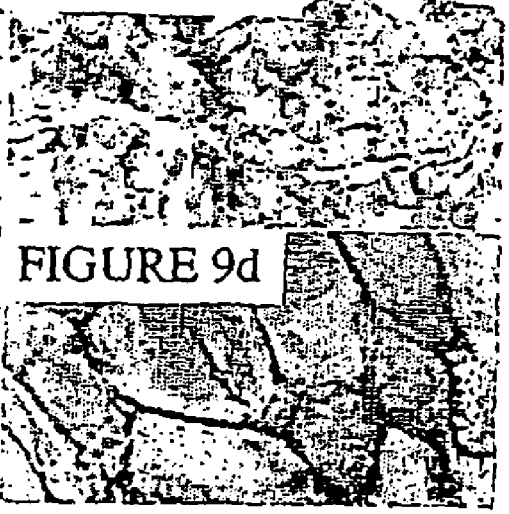

FIGURE 10a
FIGURE 10b
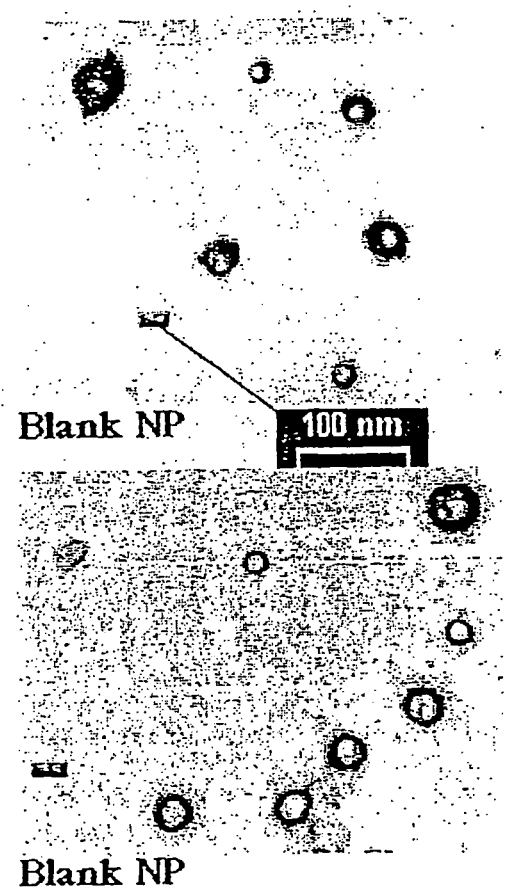
Blank NP
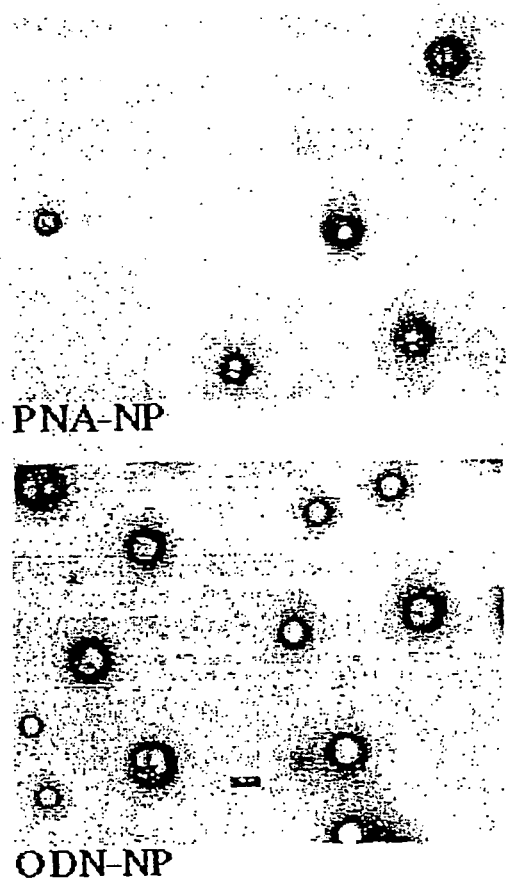
PNA-NP
Blank NP
ODN-NP
FIGURE 10c
FIGURE 10d

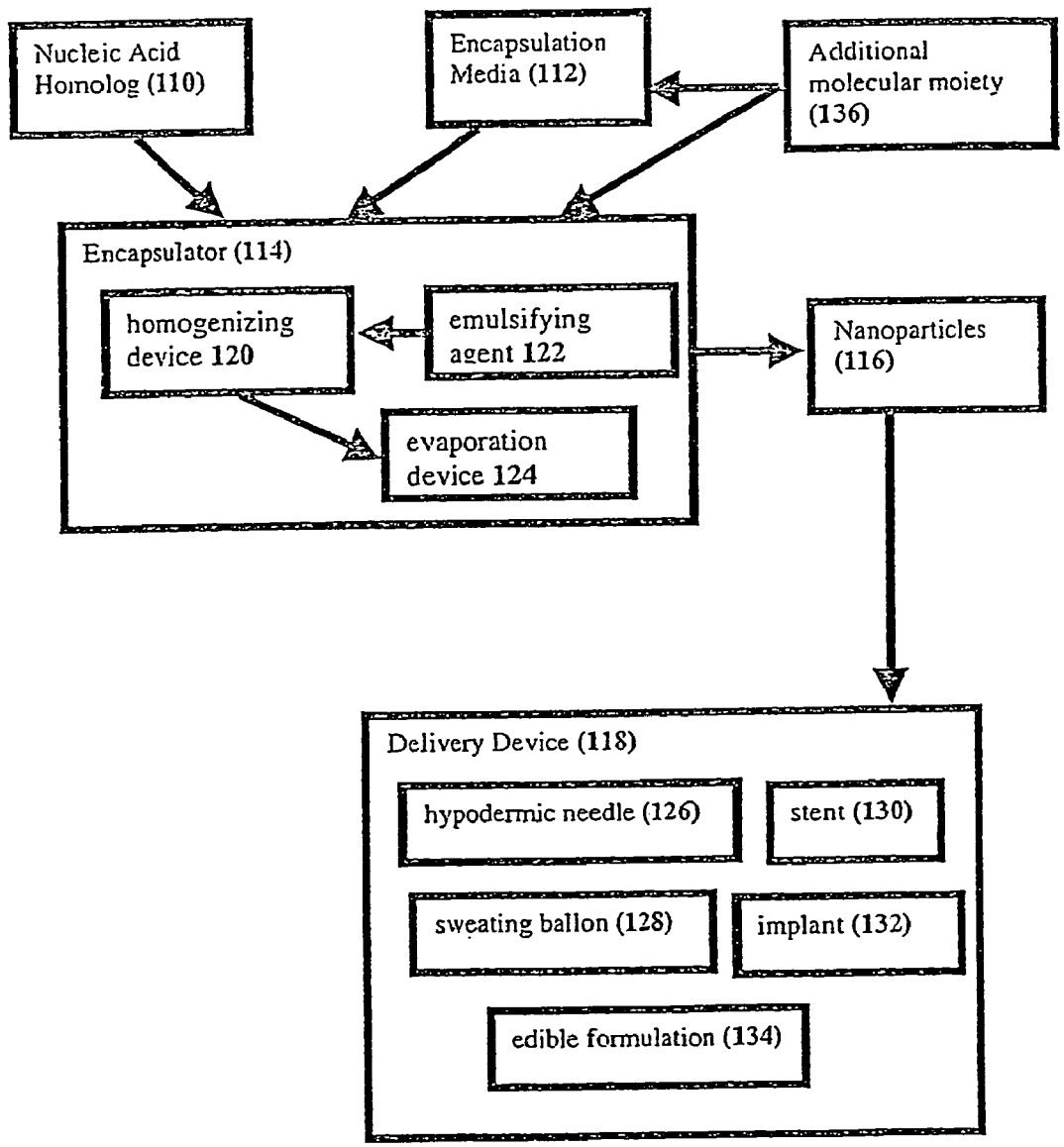

FIGURE 18    200
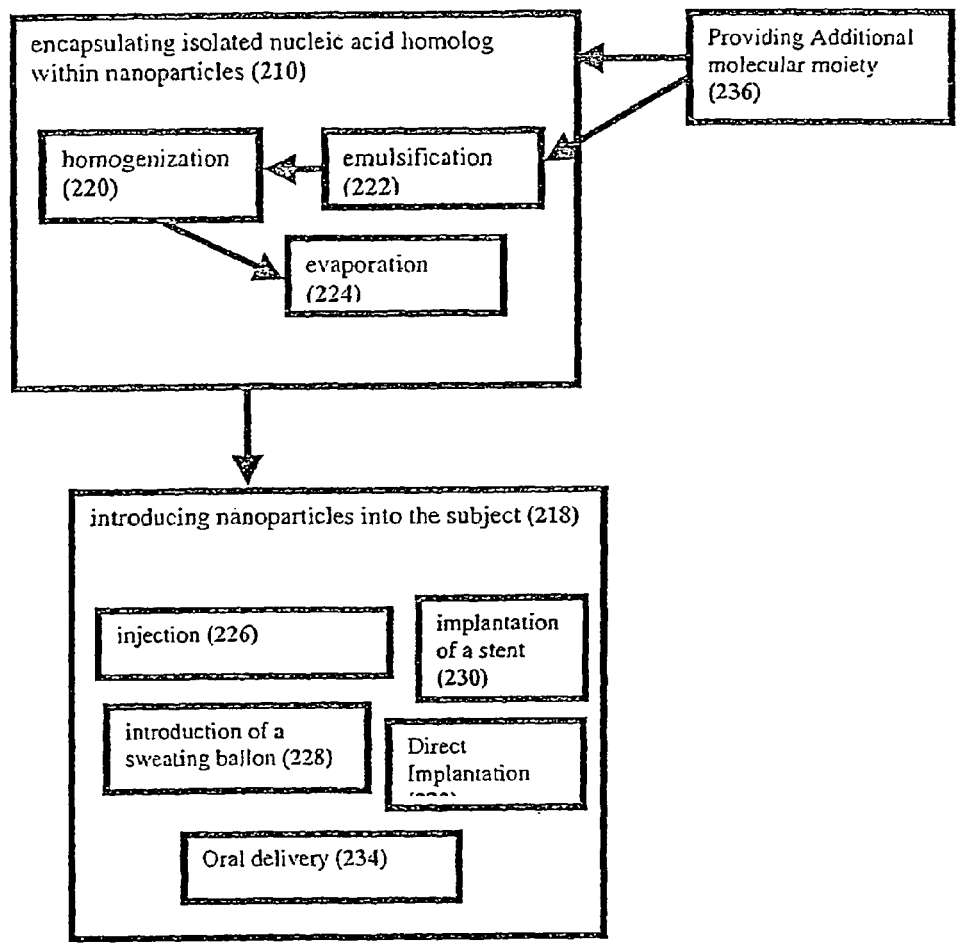
FIGURE 19    300
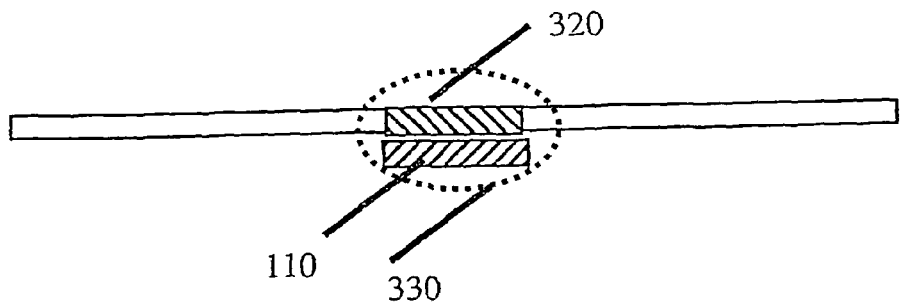

SEQUENCE LISTING

<160> NUMBER OF SEQ ID NOS: 25

<210> SEQ ID NO 1
<211> LENGTH: 18
<212> TYPE: DNA
<213> ORGANISM: Artificial
<220> FEATURE:
<223> OTHER INFORMATION: synthetic oligonucleotide; partially phosphorothiated

<400> SEQUENCE: 1
cggagagagg ccgtcgat                                                                   18

<210> SEQ ID NO 2
<211> LENGTH: 18
<212> TYPE: DNA
<213> ORGANISM: artificial
<220> FEATURE:
<223> OTHER INFORMATION: synthetic oligonucleotide; partially phosphorothiated

<400> SEQUENCE: 2
cggagagagg ccgtcgat                                                                   18

<210> SEQ ID NO 3
<211> LENGTH: 18
<212> TYPE: DNA
<213> ORGANISM: artificial
<220> FEATURE:
<223> OTHER INFORMATION: synthetic oligonucleotide; phosphorothiated

<400> SEQUENCE: 3
cggagagagg ccgtcgat                                                                   18

<210> SEQ ID NO 4
<211> LENGTH: 18
<212> TYPE: DNA
<213> ORGANISM: artificial
<220> FEATURE:
<223> OTHER INFORMATION: synthetic oligonucleotide; phosphorthiated

<400> SEQUENCE: 4
cgggaggaag cccatggt                                                                   18

<210> SEQ ID NO 5
<211> LENGTH: 18
<212> TYPE: DNA
<213> ORGANISM: Rattus norvegicus

<400> SEQUENCE: 5
tatcactcct ggaagccc                                                                   18

<210> SEQ ID NO 6
<211> LENGTH: 18
<212> TYPE: DNA
<213> ORGANISM: Rattus norvegicus

<400> SEQUENCE: 6
ttacactcct ggacagcc                                                                   18

<210> SEQ ID NO 7
<211> LENGTH: 18
<212> TYPE: DNA
<213> ORGANISM: Homo sapiens

-continued

```
<400> SEQUENCE: 7
gagcacaggc tcgtgctg                                                   18

<210> SEQ ID NO 8
<211> LENGTH: 18
<212> TYPE: DNA
<213> ORGANISM: Homo sapiens

<400> SEQUENCE: 8
gaggtggagc tccacctg                                                   18

<210> SEQ ID NO 9
<211> LENGTH: 18
<212> TYPE: DNA
<213> ORGANISM: Homo sapiens

<400> SEQUENCE: 9
cggaagccgc atggtgtc                                                   18

<210> SEQ ID NO 10
<211> LENGTH: 18
<212> TYPE: DNA
<213> ORGANISM: Homo sapiens

<400> SEQUENCE: 10
cgggtgccgc atgaagtc                                                   18

<210> SEQ ID NO 11
<211> LENGTH: 18
<212> TYPE: DNA
<213> ORGANISM: Homo sapiens

<400> SEQUENCE: 11
agagctggca tcgcaccc                                                   18

<210> SEQ ID NO 12
<211> LENGTH: 18
<212> TYPE: DNA
<213> ORGANISM: Homo sapiens

<400> SEQUENCE: 12
agcgatggca tcgcaccc                                                   18

<210> SEQ ID NO 13
<211> LENGTH: 18
<212> TYPE: DNA
<213> ORGANISM: Homo sapiens

<400> SEQUENCE: 13
atttaagcat cttgacgg                                                   18

<210> SEQ ID NO 14
<211> LENGTH: 18
<212> TYPE: DNA
<213> ORGANISM: Homo sapiens

<400> SEQUENCE: 14
ataattgcat ctggtgac                                                   18

<210> SEQ ID NO 15
<211> LENGTH: 18
<212> TYPE: DNA
<213> ORGANISM: Mus musculus
```

```
<400> SEQUENCE: 15
tgattgcgga aaaccctg                                                18

<210> SEQ ID NO 16
<211> LENGTH: 18
<212> TYPE: DNA
<213> ORGANISM: Mus musculus

<400> SEQUENCE: 16
ttgtagcggc acaacatg                                                18

<210> SEQ ID NO 17
<211> LENGTH: 18
<212> TYPE: DNA
<213> ORGANISM: Mus musculus

<400> SEQUENCE: 17
tggaagcccc atggtgtc                                                18

<210> SEQ ID NO 18
<211> LENGTH: 18
<212> TYPE: DNA
<213> ORGANISM: Mus musculus

<400> SEQUENCE: 18
ggatagcccc atgtgtgc                                                18

<210> SEQ ID NO 19
<211> LENGTH: 18
<212> TYPE: DNA
<213> ORGANISM: Mus musculus

<400> SEQUENCE: 19
aggaagccca tggtggga                                                18

<210> SEQ ID NO 20
<211> LENGTH: 18
<212> TYPE: DNA
<213> ORGANISM: Mus musculus

<400> SEQUENCE: 20
gaagagccga gtctggga                                                18

<210> SEQ ID NO 21
<211> LENGTH: 18
<212> TYPE: DNA
<213> ORGANISM: Rattus norvegicus

<400> SEQUENCE: 21
tggaagcccc atggtgcc                                                18

<210> SEQ ID NO 22
<211> LENGTH: 18
<212> TYPE: DNA
<213> ORGANISM: Rattus norvegicus

<400> SEQUENCE: 22
tggaagactc gcggtccc                                                18

<210> SEQ ID NO 23
<211> LENGTH: 18
<212> TYPE: DNA
<213> ORGANISM: Rattus norvegicus
```

```
<400> SEQUENCE: 23
tcctcgctgt cctgttat                                                 18

<210> SEQ ID NO 24
<211> LENGTH: 18
<212> TYPE: DNA
<213> ORGANISM: Rattus norvegicus

<400> SEQUENCE: 24
ttcccgctgc tcgtttat                                                 18

<210> SEQ ID NO 25
<211> LENGTH: 23
<212> TYPE: PRT
<213> ORGANISM: Homo sapiens

<400> SEQUENCE: 25

Ser Val Lys Ala Gln Trp Lys Lys Asp Lys His Arg His Cys Arg Leu
1               5                   10                  15

Thr Arg Lys Arg Gly Leu Lys
            20
```

NANOPARTICLES CONTAINING POLYMERIC NUCLEIC ACID HOMOLOGS

The present application is a 371 of PCT/IL02/00985 filed on Dec. 5, 2002, which claims benefit of 60/335,837 filed Dec. 5, 2001.

FIELD AND BACKGROUND OF THE INVENTION

The present invention relates to nanoparticles containing polymeric nucleic acid homologs, pharmaceutical compositions and articles of manufacture containing same and methods of use thereof and, more particularly, to delivery of functional polymeric nucleic acid homologs to living cells.

There is a long standing interest in development of new methods for gene delivery that do not require viral vectors which are typically associated with immunogenicity, oncogenesis and unknown long-term effects (Mahato et al. (1999) Adv Genet 41: 95-156). Development of these new methods has the potential to provide pharmaceutical formulations to deliver genes and to compete against conventional pharmaceutical, biological and surgical therapies, by offering increased efficacy, safety, regulatory compliance and reduced cost (Ledley (1994) Curr Opin Biotechnol 5: 626-636).

Unfortunately, known nonviral gene delivery systems or "artificial viruses" typically share two inherent disadvantages. The first disadvantage is that they are less effective than real viruses in terms of DNA delivery capacity. The second disadvantage is that they imitate biological functions of viruses and are therefore likely to cause an immune response and/or oncogenesis. Known nonviral gene delivery systems differ fundamentally from viral systems in terms of their composition, therapeutic profile, clinical risks and environmental safety (Ledley (1995) Hum Gene Ther 6: 1129-1144; Rolland (1998) Crit Rev Ther Drug Carrier Syst 15: 143-198 and Roy et al. (1999) Nature Med 5: 387-391). Cationic liposomes are one type of nonviral gene delivery systems (Chonn & Cullis (1998) AdvDrug Del Rev 30: 73-83. Cationic liposomes have as inherent disadvantages low in-vivo transfection efficiency and moderate cell toxicity. Further, cationic liposomes are subject to inactivation by serum and extracellular matrix components, and often form aggregates. These disadvantages render them unsuitable for use in many in-situ applications, although they are often employed in tissue culture.

Polymeric and collagen-based matrices are an additional type of nonviral gene delivery systems (Bonadio et al. (1998) Adv Drug Del Rev 33: 53-69. Labhasetwvar et al. (1998) JPharm Sci 1998; 87:1347-1350 and Shea et al (1999) Nat Biotechnol 17: 551-554). Matrices of these types are suitable only for local delivery. Further, they exhibit low in-vivo transfection efficiency, and large amounts of pDNA are required in order to achieve a biological effect. These disadvantages render them unsuitable for use in many in-situ applications, especially if a systemic effect is required or if local delivery is impractical.

Biodegradable and non-biodegradable polymer based particles are an additional type of nonviral gene delivery systems (Smith et al. (1997) Adv Drug Del Rev 26: 135-150; Mathiowitz et al. (1997) Nature 386: 410-414; Hedley et al. (1998) Nature Med 4: 365-368; Leong et al. (1998) J Control Rel 53: 183-193 and Labhasetwar et al. (1999) Colloids and Surfaces B:Biointerfaces 16: 281-290). While it is recognized that delivery via polymeric particles has the potential to offer increased resistance to nuclease degradation, control in dosing, sustained release of plasmid DNA (pDNA), and prolonged gene action (Ledley (1996) Pharm Res 13: 1595-1614 and Jong et al. (1997) J Control Rel 1997; 47: 123-134), this potential has not been realized in any specific clinical context to date.

Polymeric particle based systems are also theoretically able to control release rate kinetics, so as to provide a timed release of pDNA, and are therefore theoretically suitable in situations when long-term localized gene expression meets the aims of therapy. Unfortunately, development of sustained release gene delivery systems has been slow and fraught with technical difficulties (Labhasetwar et al. (1998) J Pharm Sci 87: 1347-1350; Shea et al. (1999) Nat Biotechnol 17: 551-554; Labhasetwar et al. (1999) Colloids and Surfaces B:Biointerfaces 16: 281-290; Jong et al. (1997) J Control Rel 47: 123-134; Luo et al. (1999) Pharm Res 16:1300-1308 and Ando et al. (1999) J Pharm Sci 88: 126130). Matrices of these types are suitable only for local delivery. Further, they exhibit low in-vivo transfection efficiency, and large amounts of pDNA are required in order to achieve a biological effect. These disadvantages render them unsuitable for use in many in-situ applications, especially if a systemic effect is required or if local delivery is impractical.

Thus, the primary obstacle preventing development of efficient non-viral gene delivery systems remains development of sufficient transfection efficiency. To date, direct transfection efficiency of pDNA from nanoparticles encapsulating pDNA (rather than transfection evaluation of) has not been reported. Instead, reported results have been in terms of transfection efficiency of pre-released pDNA. Similarly, absorbtion of pDNA containing particles and/or expression of pDNA encoded genes over prolonged periods of time has not been reported.

One proposed application for nanoparticle based gene delivery systems is antisense therapy. The purpose of antisense therapy is to inhibit expression of a particular gene. This may be achieved by using oligodeoxynucleotide (ODN), double stranded DNA peptide nucleic acids (PNA), antisense RNA, double stranded RNA or ribozymes. Antisense therapy works by inhibiting expression of a selected gene at the level of translation (Deshpande et al. (1996) Pharmaceutical News 3). For any protein or peptide to be synthesized, the gene encoding it must be transcribed from DNA to mRNA. In some cases the mRNA is processed, for example by splicing or cleavage. The mRNA must then be translated into protein. Antisense therapy relies upon down regulation of the functional protein by preventing mRNA translation or processing. This is typically achieved by destabilizing selected mRNA transcripts by hybridizing them with a complementary nucleic acid (or nucleic acid analog) sequence. The hyridized double stranded molecule is then subject to enzymatic degradation (e.g. with RNAase H) within the cell. Alternately, the hybridized double stranded molecule prevents mRNA processing because a recognition site for an enzyme is hidden by the complementary second strand. Alternately, the complementary second strand blocks the translation initiation codon of the transcript and prevents translational initiation (translational arrest). Phosphorothioated oligodeoxyribonucleotides (ODNs) stretches have been employed for sequence specific hybridization.

An alternate method of inhibiting a specific gene is transcriptional inhibition or the antigen approach. This may be achieved by use of PNAs (FIG. 1) which recognize and invade double-stranded DNA (triplex formation) in a sequence specific manner thereby preventing transcription. Alternately, PNA's may be employed as mRNA binding reagents in place of ODNs in antisense and antigen therapy as described above.

While the methods described hereinabove are theoretically recognized, their implementation has been problematic.

ODNs are usually prepared with a nuclease resistant derivatization such as phosphorothioate (PT-ODNs, FIG. 1) in order to retard enzymatic degradation and permit their activity in-vivo. Unfortunately, once in-vivo stability was achieved, even non-specific oligonucleotide sequences (PT-ODNs) have demonstrated unexpected potent activity (Stein (2001) J. Clin. Invest. 108:641-4). Furthermore, therapeutic use of ODNs has been hampered by their inherently low cellular permeability which is generally attributed to large molecular size and high charge density. The observed activity of ODNs in-vivo is therefore attributed to cellular uptake via an energy-dependent endocytosis (Akhtar et al. (1992) Trends Cell Biol. 2:139-144). These problems with ODNs have led to the development of viral vectors, liposomes and receptor-mediated endocytosis (Mahato et al. (1997) J. Drug Target. 4:337-357). Each of these delivery strategies has inherent disadvantages as detailed hereinabove and hereinbelow.

In summary, currently available viral gene delivery vectors share, as inherent disadvantages, a number of safety related problems including, but not limited to, immunogenicity of the vectors, formation of replication-competent viruses in patients and possible presence of contaminating agents in viral vector preparations. Additional safety concerns are raised by the possibility of insertional mutagenisis and transmission of viral and other exogenous DNA to the germ line of patients undergoing treatment. Additional disadvantages result from the physical limitations imposed by the virus particle. These additional disadvantages include lack of tissue specificity, limited insert size, and difficulties in manufacturing (Romano et al. (2000) Stem Cells. 18:19-39; Romano et al. (1999) Stem Cells. 17:191-202, Dani (1999) Braz. J. Med. Biol. Res. 32:133-145).

In summary, currently available non-viral gene delivery vectors share, as inherent disadvantages, low transfection efficiency, lack of specific targeting capability, transient expression and an immune response elicited from the unmethylated CpG islands of the bacterial DNA (Romano et al. (2000) Stem Cells. 18:19-39; Li et al. (2000). Gene Ther. 7:31-34; Rolland (1998) Crit. Rev. Ther. Drug Carrier Syst. 15:143-198). Liposomes have additional disadvantages as detailed herein above. Further, currently available non-viral gene delivery vectors rely upon receptor-mediated endocytosis which is largely due to poly-1-lysin as the gene vector. The use of poly-1-lysin is problematic due its polydispersity and heterogenicity which contribute to low in-vivo transfection efficiency.

While adsorbtion of ODNs onto polyalkylcyanoacrylate nanoparticles (Lambert et al. (2001) Adv. Drug. Del Rev. 47(1):99-112) enhances stability against nucleases and leads to a more ideal cellular distribution, problems of efficient cellular delivery, lysosomal degradation and lack of specificity have provided serious obstacles for therapeutic use of such particles.

Peptide nucleic acids (PNA) are ODN analogs in which the sugar-phosphate moiety has been replaced by 2-aminoethyl glycine units linked by amide bounds (FIG. 2 and Nielsen (2000) Curr. Opin. Mol. Ther. 2:282-7). The bases are attached to the backbone by methylene carbonyl linkage. Due to the backbone neutrality, PNA oligomers hybridize to complementary DNA and RNA faster and with greater affinity by Watson-Crick's base pairing (Ray & Norden (2000) FASEB J. 14:1041-60 and Soomets et al. (1999) Front. Biosci. 1:4D782-6). In addition, PNA are better at discriminating between base pair mismatches and have less affinity for cellular proteins than PT-ODNs (Doyle D F et al. (2001) Biochemistry. 40:53-64). Despite these advantages, PNAs are currently considered to be of only limited suitability for therapeutic use because of their poor cellular incorporation (Dean (2000) Adv. Drug Del. Rev. 44:81-95).

One medical problem which may be amenable to antisense therapy is restenosis after percutaneous transluminal coronary angioplasty. Restenosis is the main complication after percutaneous transluminal coronary angioplasty and accounts for 35 to 40% of post procedure complications (Chorny et al. (2000) Crit. Rev. Ther. Drug. Carrier. Syst. 17:249-84). The migration and proliferation of medial vascular smooth muscle cells (SMC) are thought to be the main components in neointimal formation. Signal transduction through the platelet-derived growth factor (PDGF)/PDGF receptors system is involved in the process of post-angioplasty restenosis. A sustained inhibition of this pathway is therefore a promising strategy which has gained considerable research attention as a potential means to effectively control neointimal formation (Fishbein et al. (2000) Arterioscler Thromb Vasc Biol. 20:667-76; Fishbein et al. (2000) J. Controlled Release. 65:221-9; Hughes et al. (1996) Gen. Pharmac. 27:1079-1089; Noiseux et al. (2000) Circ. 102:1330-1336 and Sirois et al. (1997) Circulation. 95:669-676). However, no significant progress has been made in exploiting the PDGF/PDGF receptors system as a point of intervention for prevention of restenosis. This lack of progress results from an emphasis on drug based, ae opposed to gene based, therapy. Gene therapy has the potential to be far mor specific by use of, for example, promoter specific sequences or cell specific ligands.

Antisense therapy also has potential utility in treatment of cell proliferation disorders. For example, altering intimal hyperplasia has been reported using AS-ODNs to inhibit growth-regulatory or cell-cycle genes (c-myb, c-myc, PCNA, cdc2, and cdk2) involved in SMC proliferation Sirois et al. (1997) Circulation. 95:669-676. and Villa et al. (1995) Circ. Res. 76:505-513. However, all the AS-ODNs used were fully phosphorothioated analogs. Although fully phosphorothioated ODNs have increased stability and nuclease resistance, they display high affinity for various cellular proteins, resulting in nonspecific effects. Furthermore, high concentrations of phosphorothioated oligodeoxynucleotides (PT-ODNs) inhibit DNA polymerases and RNase H, which may render them ineffective as antisense agents (Stein (2001) J. Clin. Invest. 108:641-4).

The most common problems encountered in prior art gene therapy protocols are poor efficacy and immune response of the host to the vector. Poor efficacy may result from failure of the delivered material to enter cells, to integrate into the genome, or to be expressed at appropriate levels. In addition, response over the course of time is often poor. This means that readministration, which might be advantageous, is often problematic due to the abovementioned immune response.

There is thus a widely recognized need for, and it would be highly advantageous to have, nanoparticles containing polymeric nucleic acid homologs, pharmaceutical compositions and articles of manufacture containing same and methods of use thereof devoid of the above limitations.

SUMMARY OF THE INVENTION

According to one aspect of the present invention there is provided a system for altering an expression level of at least one gene within at least one cell of a subject. The system includes: (a) an encapsulation media includes a biodegradable polymer; (b) an encapsulator designed and constructed to encapsulate an isolated nucleic acid homolog sequence within nanoparticles of the encapsulation media; (c) a delivery device designed and constructed to introduce the nanoparticles containing the isolated nucleic acid homolog sequence into the subject. The nanoparticles are capable of releaseing the isolated nucleic acid homolog sequence over an extended period of time.

According to another aspect of the present invention there is provided a method of sustained delivery and release of a nucleic acid homolog within a subject. The method includes: (a) encapsulating a nucleic acid homolog within nanoparticles; and (b) introducing the nanoparticles into the subject.

According to yet another aspect of the present invention there is provided a system for treating a medical condition of a subject by sustained delivery of a nucleic acid homolog. The system includes: (a) an encapsulation media includes a biodegradable polymer; (b) an isolated nucleic acid homolog sequence designed to alleviate symptoms of the medical condition; (c) an encapsulator designed and constructed to encapsulate within nanoparticles the isolated nucleic acid homolog sequence within the encapsulation media; (d) a delivery device designed and constructed to introduce the nanoparticles into the subject where the isolated nucleic acid homolog sequence is released over an extended period of time.

According to still another aspect of the present invention there is provided a method of treating a medical condition of a subject by sustained delivery of a nucleic acid homolog. The method includes: (a) encapsulating an isolated nucleic acid homolog sequence designed to alleviate symptoms of the medical condition within an encapsulation media so that nanoparticles are formed; and (c) delivering the nanoparticles into the subject where the isolated nucleic acid homolog sequence is released over an extended period of time.

According to an additional aspect of the present invention there are provided nanoparticles capable of delivery of an encapsulated molecule into a living cell. The nanoparticles include: (a) an encapsulation media includes a biodegradable polymer; and (b) an isolated nucleic acid homolog sequence encapsulated with the encapsulation medium. The nanoparticles are capable of releasing the isolated nucleic acid homolog sequence over an extended period of time.

According to yet an additional aspect of the present invention there is provided a pharmaceutical composition for treating a medical condition. The composition includes a therapeutically effective amount of nanoparticles capable of delivery of an encapsulated molecule into a living cell, the nanoparticles constituting an active ingredient of the composition. The nanoparticles include (i) an encapsulation media including a biodegradable polymer; and (ii) an isolated nucleic acid homolog sequence encapsulated within the encapsulation media. The nanoparticles are capable of releasing the isolated nucleic acid homolog sequence over an extended period of time. The composition further includes a physiologically acceptable carrier and/or excipient.

According to still an additional aspect of the present invention there is provided an article of manufacture including packaging material and a pharmaceutical composition identified for treatment of a medical condition contained within the packaging material. The pharmaceutical composition includes a therapeutically effective amount of nanoparticles capable of delivery of an encapsulated molecule into a living cell, the nanoparticles constituting an active ingredient of the composition. The nanoparticles include (i) an encapsulation media including a biodegradable polymer; and (ii) an isolated nucleic acid homolog sequence encapsulated within the encapsulation media. The nanoparticles are capable of releasing the isolated nucleic acid homolog sequence over an extended period of time. The composition further includes a physiologically acceptable carrier and/or excipient.

According to a further aspect of the present invention there is provided a method of blocking expression of a specific nucleic acid sequence. The method includes administering an isolated nucleic acid homolog sequence designed and constructed to specifically hybridize to at least a portion of the specific nucleic acid sequence so that a multistranded complex is formed.

According to further features in preferred embodiments of the invention described below, the biodegradable polymer includes PLGA [poly(DL-lactide-co-glycolide)].

According to still further features in the described preferred embodiments the encapsulation media further includes a salt of a divalent cation.

According to still further features in the described preferred embodiments the divalent cation is calcium.

According to still further features in the described preferred embodiments the encapsulator includes a homogenizing device, at least one emulsifying agent and an evaporation device.

According to still further features in the described preferred embodiments the delivery device is selected from the group consisting of a hypodermic needle, a sweating balloon, a stent, an implant and an edible formulation.

According to still further features in the described preferred embodiments the nucleic acid homolog includes at least one compound selected from the group consisting of DNA (deoxyribonucleic acid), RNA (ribonucleic acid), PNA (peptide nucleic acid) and chemical derivatives thereof. The terms "DNA" and "RNA" as used in this specification and the accompanying claims refer equally to single stranded and to double stranded molecules.

According to still further features in the described preferred embodiments the chemical derivative is a phosphorothioate derivative.

According to still further features in the described preferred embodiments the phosphorothioate derivative includes phosphorothioate linkages at only some of a set of positions available for the phosphorothioate linkages.

According to still further features in the described preferred embodiments the system further includes an additional molecular moiety miscible with the encapsulation media and designed to impart a cellular specificity to the nanoparticles.

According to still further features in the described preferred embodiments the additional molecular moiety includes a peptide.

According to still further features in the described preferred embodiments the peptide imparts to the nanoparticles a specific affinity for at least one target selected from the group consisting of an LDL receptor and a GAG-binding region of apoB-100.

According to still further features in the described preferred embodiments the peptide includes at least a functional portion of an amino acid sequence as set forth in SEQ. ID. NO. 25.

According to still further features in the described preferred embodiments the nucleic acid homolog is designed and constructed to undergo transcription to produce at least one RNA transcript within the at least one cell of the subject.

According to still further features in the described preferred embodiments the at least one RNA transcript is selected from the group consisting of an mRNA encoding at least a functional portion of an amino acid sequence and an antisense sequence capable of hybridizing with at least one mRNA transcript in the at least one cell of the subject.

According to still further features in the described preferred embodiments the nucleic acid homolog is designed and constructed hybridize to at least one endogenous nucleic acid sequence in the at least one cell of the subject.

According to still further features in the described preferred embodiments the at least one endogenous nucleic acid sequence is selected from the group consisting of at least a portion of an mRNA transcript and a genomic DNA sequence.

According to still further features in the described preferred embodiments the encapsulating is within a biodegradable composition includes PLGA [poly(DL-lactide-co-glycolide)] polymers.

According to still further features in the described preferred embodiments the encapsulating includes homogenization, emulsification and evaporation.

According to still further features in the described preferred embodiments the introducing the nanoparticles into the subject is accomplished by a method selected from the group consisting of injection, introduction of a sweating balloon, implantation of a stent, direct implantation of the nanoparticles within the subject and oral delivery. The term "injection" as used in this specification and the accompanying claims refers to any route of injection including, but not limited to intravenous (iv), intrarterial (ia), subdermal, intramuscular, intraperitoneal (ip) and intraluminal.

According to still further features in the described preferred embodiments the method further includes phosphorothioation of the nucleic acid homolog.

According to still further features in the described preferred embodiments the phosphorothioation includes phosphorothioation at only some of a set of positions available for the phosphorothioation.

According to still further features in the described preferred embodiments the method further includes providing on the nanoparticles an additional molecular moiety designed to impart a cellular specificity to the nanoparticles.

According to still further features in the described preferred embodiments the additional molecular moiety includes a peptide.

According to still further features in the described preferred embodiments the method further includes designing the peptide to impart to the nanoparticles a specific affinity for at least one target selected from the group consisting of an LDL receptor and a GAG-binding region of apoB-100.

According to still further features in the described preferred embodiments the at least one RNA transcript is selected from the group consisting of an mRNA encoding at least a functional portion of an amino acid sequence and an antisense sequence capable of hybridizing with at least one mRNA transcript in at least one cell of the subject.

According to still further features in the described preferred embodiments the nucleic acid homolog is designed and constructed hybridize to at least one endogenous nucleic acid sequence in the at least one cell of the subject.

According to still further features in the described preferred embodiments the at least one endogenous nucleic acid sequence is selected from the group consisting of at least a portion of an mRNA transcript and a genomic DNA sequence.

According to still further features in the described preferred embodiments nanoparticles of the present invention are characterized by an average particle size in the range of 200 to 700 nm, more preferably 200-400 nm (e.g. antisense ODN), alternately but also more preferably, 400-700 nm (e.g. plasmid DNA).

According to still further features in the described preferred embodiments the medical condition is selected from the group consisting of a cell proliferation disorder, an infectious disease, a genetic defect and aberrant gene regulation nucleic.

The present invention successfully addresses the shortcomings of the presently known configurations by providing means to deliver nucleic acid homologs to living cells with high efficiency over a period of time.

According to still further features in the described preferred embodiments the method serves to deliver acid homologs to living cells with high efficiency over a period of time.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 2a, 2b and 2c are Photomicrographs of pDNA (alkaline phosphatase) loaded polymeric (PLGA) nanoparticles (NP). FIG. 2a is a pair of scanning electron micrographs of Blank-NP (1) and pDNA-NP (2). Gold coating (200 s), magnification 5K, 30 kV, bar=10 µm. FIG. 2b is a pair of transmission electron micrographs of Blank-NP (1), and pDNA-NP (2). Phospho-tungstic acid (1%) negative staining, magnification ×140K. FIG. 2c is a pair of fluorescence micrographs of blank-NP (1) and pDNA-loaded NP (2) labeled with Et-Br (3 h incubation in 1 mg/ml solution); bar, 10 µm.

FIG. 3 is a graph illustrating cumulative release (% of amount loaded) of pDNA from pDNA-loaded nanoparticles as a function of time. Release was measured in TE buffer pH 7.4, 37° C. (mean±s.e.m., n=4). Inset shows times shorter than one day.

FIGS. 4a and 4b are photographs of agarose gel electrophoresis of pDNA released from polymeric nanoparticles. FIG. 4a shows lane 1, λ HindIII marker; lane 2, naked pDNA; lane 3, pDNA released from NP. FIG. 4b shows lane 1, λ HindIII marker; lane 2, restriction enzyme digestion of naked pDNA; lanes 3-5, restriction enzyme digestion of pDNA released from NP (formulations NP-1, 2 and 3, respectively, see Table 1). The ratio between relaxed (nicked) to supercoiled conformation of pDNA released from the NP was increased from 30:70 to 60:40% in comparison with control pDNA (A).)

FIGS. 6a, 6b and 6c are confocal micrographic images of NIH 3T3 cells transfected with fluorescent-labeled pDNA encapsulated in NP. The encapsulated pDNA (20 μg) was labeled with TOTO-1 (1 μm), a cell-impermeable fluorescent probe. Both blank-NP and naked plasmid (not shown) exhibited very low fluorescence and were subtracted as background. An overview of uptake and localization is shown in FIG. 6a. FIG. 6b shows nuclear DNA, and perinuclear localization of NP and released pDNA. FIG. 6c is a perinuclear nanoparticle at higher magnification. Note the sparse fluorescence of released pDNA in the nuclei (white arrows), and perinuclear localization of released DNA and pDNA-NP (black arrows). The pDNA (not a sphere shape) detected inside the cell could result only from pDNA released intracellularly following internalization of nanoparticle(s) containing pDNA. since TOTO-1 labeled DNA is cell impermeable.

FIGS. 9a, 9b, 9c and 9d illustrate histochemical staining of alkaline phosphatase (AP) in tibial muscle sections of rats treated with pDNA-NP (formulation NP 1). Sections shown are of saline (a), pDNA (b), and pDNA-NP (cd). Muscles were harvested 7 days after injection, sectioned, fixed, and stained using FRV-alkaline dye mixture for AP, and counterstained with hematoxylin solution. Red spots indicate AP recombinant protein, and the nucleus is stained in blue. Magnification ×20(a-c), and ×40 (d).

FIGS. 10a-d present transmission electron micrographs of ODN and PNA loaded polymeric (PLGA) nanoparticles (NPs). Phospho-tungstic acid (1%) negative staining, magnification ×140K. Note the spherical morphology of the NPs (ca. 300 nm). (a and c) blank NP; (b) PNA-NP; (d) ODN-NP.

FIG. 17 is a diagram illustrating components of a system according to the present invention.

FIG. 18 is a simplified flow diagram of steps in methods according to the present invention.

FIG. 19 is a cartoon illustrating formation of a multistrand complex in conjunction with a method according to the present invention.

DESCRIPTION OF THE PREFERRED EMBODIMENTS

Figure 1A:
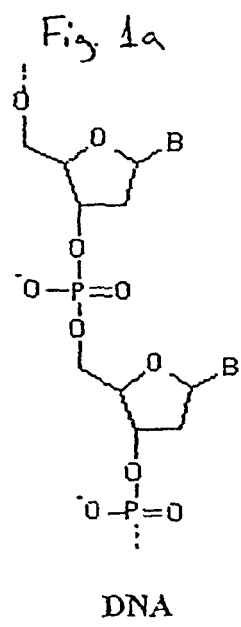
FIGS. 1a, 1b, and 1c are diagrams of chemical structures of the DNA homologs DNA, PT-ODN and PNA respectively.
Figure 1B:
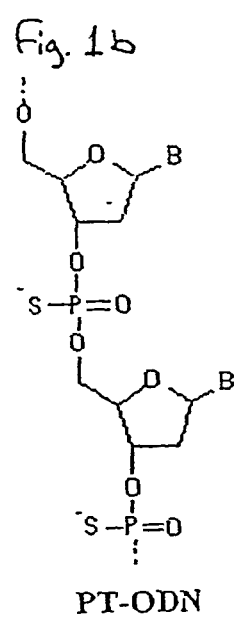
Figure 1C:
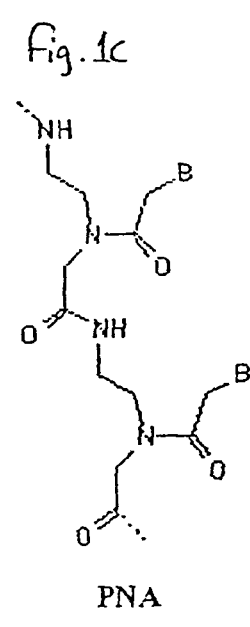

The present invention is of nanoparticles containing polymeric nucleic acid homologs, pharmaceutical compositions and articles of manufacture containing same and methods of use thereof which can be employed for delivery of functional polymeric nucleic acid homologs to living cells. Specifically, the present invention can be used to deliver functional polymeric nucleic acid homologs to living cells over an extended period of time without adversely affecting the cells. Further, the present invention permits repeated administration of functional polymeric nucleic acid homologs to living cells without provoking an immune response in a host The term "nucleic acid homolog" as used in this specification and the accompanying claims includes, but is not limited to, DNA (deoxyribonucleic acid), RNA (ribonucleic acid), PNA (peptide nucleic acids) and chemical derivates thereof (e.g. FIG. 1). Chemical derivatives include molecules with side chains and/or substitutions such as, for example phosphorothioate-DNA (PT-DNA). As indicated hereinabove, the nucleic acid homologs may in some cases be single stranded and in other cases double stranded.

The phrase "extended period of time" as used in this specification and the accompanying claims preferably refers to a period in excess of three days and more preferably refers to a period of approximately 30 days.

The principles and operation of nanoparticles containing polymeric nucleic acid homologs, pharmaceutical compositions and articles of manufacture containing same and methods of use thereof according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The present invention is preferentially embodied by a system 100 (FIG. 17) for altering an expression level of at least one gene within at least one cell of a subject. The phrase "altering an expression level of at least one gene" as used in this specification refers equally to upregulation and to downregulation of levels of at least a functional portion of a peptide or protein. The peptide or protein may be exogenous or endogenous. Regulation may be accomplished, for example, by regulating transcriptional initiation, transcript stability, post-transcriptional processing (e.g. splicing or cleavage), translation initiation, post transcriptional processing or binding of at least a portion of a translation product (e.g. with an antibody or functional portion thereof or a receptor or a ligand). Thus, "expression" as used herein, includes transcription, translation, and stability as well as activity.

System 100 includes an encapsulation media 112 including a biodegradable polymer. The biodegradable polymer preferably includes PLGA [poly(DL-lactide-co-glycolide)]. More preferably, the biodegradable polymer is composed primarily of PLGA. Most preferably, PLGA is the only polymeric component of encapsulation media 112. Encapsulation media 112 may further include a salt of a divalent cation such as, for example, calcium. Addition of divalent cations serves to improve the biological properties of resultant nanoparticles 116.

System 100 further includes an encapsulator 114 designed and constructed to encapsulate an isolated nucleic acid homolog 110 sequence within nanoparticles 116 of encapsulation media 112. Nucleic acid homolog 110 may include, for example, single or double stranded DNA (deoxyribonucleic acid), single or double stranded RNA (ribonucleic acid), PNA (peptide nucleic acid), any combination thereof and chemical derivatives thereof. Chemical derivative, as used herein includes, but is not limited to, a phosphorothioate derivative. phosphorothioate derivatization may indicate, for example, insertion of phosphorothioate flinkages at only some of a set of positions available for such linkages (e.g. 3 linkages at each end of an ODN). Encapsulator 114 may include, for example, a homogenizing device 120, at least one emulsifying agent 122 and an evaporation device 124.

System 100 further includes a delivery device 118 designed and constructed to introduce the nanoparticles 116 containing isolated nucleic acid homolog sequence 110 into the subject. Nanoparticles 116 are capable of releaseing molecules of isolated nucleic acid homolog sequence 110 over an extended period of time. Delivery device 118 may be, for example a hypodermic needle 126, a sweating balloon 128, a stent 130, an implant 132 or an edible formulation 134. Use of sweating balloons 128, stents 130 or implants 132 tends to further prolong delivery of isolated nucleic acid homolog sequence 110 by releasing nanoparticles 116 from delivery device 118 over time. Each nanoparticle 116 releases molecules of isolated nucleic acid homolog sequence 110 over an extended period of time after it is incorporated into a cell.

Specificity of system 100 may be further enhanced by inclusion of an additional molecular moiety 136 miscible with encapsulation media 112 and designed to impart a cellular specificity to nanoparticles 116. Additional molecular moiety 136 may include a peptide. The peptide may be, for example, one which imparts to nanoparticles 116 a specific affinity for a target such as an LDL receptor or a GAG-binding region of apoB-100. One example of such a peptide is one which includes at least a functional portion of an amino acid sequence as set forth in SEQ. ID. NO. 25.

According to various preferred embodiments of the invention, system 100 may exert a physiologic effect on living cells in a variety of ways.

Figure 8:
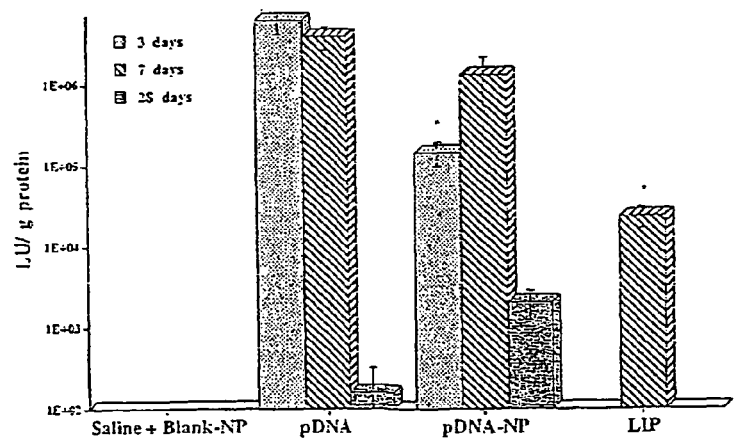
FIG. 8 is a bar graph illustrating Alkaline phosphatase (AP) expression in rat tabialis muscle 3, 7 and 28 days after a single i.m. injection of pDNA-NP (all formulations were examined, NP1 was chosen for presentation, 25 μg pDNA) in comparison to saline, blank NP, naked pDNA (2μ mg/200 μl), and LIP-pDNA (25 μg pDNA). Shown mean±s.e.m., 7<n<13, *P≦0.05.

For example nucleic acid homolog 110 may be designed and constructed to undergo transcription to produce at least one RNA transcript within the at least one cell of the subject (See examples 3 and 4 and FIGS. 8 and 9 hereinbelow. Thus, according to some preferred embodiments of the invention, the at least one RNA transcript may be an mRNA encoding at least a functional portion of an amino acid sequence (e.g. alkaline phosphatase). Thus, the present invention may be employed to provide transient immunity without use of antigens by introducing an isolated nucleic acid homolog sequence 110 encoding at least a functional portion of an antibody. According to some preferred embodiments of the invention, the nanoparticles deliver a nucleic acid homolog encoding at least a functional portion of an antibody. The term "antibody" as used in this invention includes intact molecules as well as functional fragments thereof, such as Fab, F(ab')$_2$, and Fv that are capable of binding to macrophages. These functional antibody fragments are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference).

As used in this invention, the term "epitope" means any antigenic determinant on an antigen to which the paratope of an antibody binds. Epitopic determinants usually consist of chemically active surface groupings of molecules such as amino acids or carbohydrate side chains and usually have specific three dimensional structural characteristics, as well as specific charge characteristics.

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5 S fragment denoted F(ab')$_2$. This fragment can be further cleaved using a thiol reducing agent, and optionally a blocking group for the sulfhydryl groups resulting from cleavage of disulfide linkages, to produce 3.5 S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

Humanized forms of non-human (e.g., murine) antibodies are chimeric molecules of immunoglobulins, inmmunoglobulin chains or fragments thereof (such as Fv, Fab, Fab', F(ab').sub.2 or other antigen-binding subsequences of antibodies) which contain minimal sequence derived from non-human inmmunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human inmmunoglobulin consensus sequence. The humanized antibody optimally also will comprise at least a portion of an immunoglobulin constant region (Fc), typically that of a human immunoglobulin [Jones et al., Nature, 321:522-525 (1986); Riechlmann et al., Nature, 332:323-329 (1988); and Presta, Curr. Op. Struct. Biol., 2:593-596 (1992)].

Methods for humanizing non-human antibodies are well known in the art. Generally, a humanized anitibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boemer et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in the following scientific publications: Marks et al., Bio/Technology 10, 779-783 (1992); Lonberg et al., Nature 368 S56-859 (1994); Morrison, Nature 368 812-13 (1994); Fishwild et al., Nature Biotechnology 14, 845-51 (1996); Neuberger, Nature Biotechnoloy 14, 826 (1996); Lonberg and Huszar, Intern. Rev. Immunol. 13 65-93 (1995).

Alternately, or additionally, isolated nucleic acid homolog sequence 110 may include a ribozyme sequence or an expression vector encoding a ribozyme. Ribozymes are readily synthesizable using solid phase oligonucleotide synthesis.

Ribozymes are being increasingly used for the sequence-specific inhibition of gene expression by the cleavage of mRNAs encoding proteins of interest [Welch et al., "Expression of ribozymes in gene transfer systems to modulate target RNA levels." Curr Opin Biotechnol. October 1998; 9(5):486-96]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., "Ribozyme gene therapy for hepatitis C virus infection." Clin Diagn Virol. Jul. 15, 1998; 10(2-3):163-71.]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

According to alternate preferred embodiments of the invention the at least one RNA transcript may be an antisense sequence capable of hybridizing with at least one mRNA transcript in the at least one cell of the subject.

Alternately, or additionally, nucleic acid homolog 110 may be designed and constructed to hybridize to at least one endogenous nucleic acid sequence in the at least one cell of the subject. According to various preferred embodiments of the invention, the at least one endogenous nucleic acid sequence may be, for example, at least a portion of an mRNA transcript (see examples 10, 11 and 12 hereinbelow) or a genomic DNA sequence.

Historically, use of antisense oligonucleotides to specifically block transcription of designated mRNA's or to specifically hybridize to a selected genomic DNA sequence has required solution of two problems.

The first problem is delivery of the antisense oligonucleotide into the cytoplasm or nucleus of the appropriate cells. The disclosed nanoparticles of the present invention provide an elegant solution to this problem, at the same time permitting continued delivery of isolated sequence of nucleic acid homolog 110 over an extended period of time.

The second problem is design of an oligonucleotide which binds the designated mRNA within cells in a way which inhibits translation. Intensive research has produced a means of predicting efficiency of specific oligonucleotides using an in vitro system (Matveeva et al. (1998) *Nature Biotechnology* 16, 1374-1375). At the same time, development of an algorithm for identifying those sequences with the highest predicted binding affinity for their target mRNA based on a thermodynamic cycle that accounts for the energetics of structural alterations in both the target mRNA and the oligonucleotide had been developed (Walton et al. (1999) Biotechnol Bioeng 65(1):1-9). This algorithm enabled scientist to successfully design antisense oligonucleotides for rabbit beta-globin (RBG) and mouse tumor necrosis factor-alpha (TNFalpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

Prediction of ODN sequences capable of binding a DNA sequence is mores straightforward and is routinely performed in the laboratory by a number of commercially available computer software packages such as:

Oligocalculator 3.02, supplied by Northwestern University, Chicago Ill. (http://www.basic.nwu.edu/biotools/oligocalc.html) or Oligodesigner, supplied by applied biosystems (http//www.appliedbiosystems.com/cgi-bin/calculator/ab_configured/oligodesigner/designer.cgi)

Use of PNAs assures that antisense oligomers hybridize to complementary DNA or RNA faster and with greater affinity by Watson-Crick's base pairing (Ray & Norden (2000) *FASEB J.* 14:1041-60 and Soomets et al. (1999) *Front. Biosci.* 1:4D782-6). In addition, PNA are better at discriminating between base pair mismatches and have less affinity for cellular proteins than PT-ODNs (Doyle D F et al. (2001) *Biochemistry.* 40:53-64). Despite these advantages, PNAs were previously considered to be of only limited suitability for therapeutic use because of their poor cellular incorporation (Dean (2000) *Adv. Drug Del. Rev.* 44:81-95). Nanoparticles 116 of the present invention serve as an enabling technology which permits the theoretical potential of PNAs to find application in solving clinical problems.

Thus, the current consensus is that recent developments in the field of antisense technology which, as described above, have led to the generation of highly accurate antisense design algorithms enable an ordinarily skilled artisan to design and implement antisense approaches suitable for regulating expression of known genes without having to resort to undue trial and error experimentation. Therefore, nanoparticles 116 according to various preferred embodiments of the invention as described hereinabove are expected to be employed in a wide variety of clinical settings. Those clinical settings will include, but are not limited to, use of antisense ODNs to block gene expression at the level of transcription and/or translation.

The present invention is further embodied by use of system 100 which constitutes a method 200 (FIG. 18) of sustained delivery and release of an isolated nucleic acid homolog sequence 110 within a subject. The method includes: encapsulating 210 a nucleic acid homolog 110 within nanoparticles 116. Method 200 further includes introducing 218 nanoparticles 116 into the subject. As detailed hereinabove nucleic acid homolog 110 includes one or more isolated sequences, each designed to perform a specific function within the cell. Thus nucleic acid homolog 110 may contain, for example, coding sequences, antisense sequences, regulatory elements (e.g. promoters and/or enhancers), degenerate sequences, scrambled sequences and combinations thereof. Encapsulating 210 is preferably within a biodegradable composition which includes PLGA polymers as detailed hereinabove. The process of encapsulation may include, for example homogenization 220, emulsification 222 and evaporation 224.

Introducing 218 the nanoparticles into the subject may be accomplished, for example, by a method such as of injection 226, introduction of a sweating balloon 228, implantation of a stent 230, direct implantation 232 of the nanoparticles within the subject and oral delivery 234.

Preferably, method 200 further includes providing 236 on nanoparticles 116 an additional molecular moiety (as described hereinabove) designed to impart a cellular specificity to the nanoparticles.

As described hereinabove, nucleic acid homolog 110 may be designed and constructed to undergo transcription to produce at least one RNA transcript within the at least one cell of the subject (see example 4 hereinbelow).

As described hereinabove, nucleic acid homolog 110 may be designed and constructed hybridize to at least one endogenous nucleic acid sequence (e.g. mRNa or DNA) in the at least one cell of the subject.

System 100 according to yet another aspect of the present invention there is for treating a medical condition of a subject by sustained delivery of a nucleic acid homolog. System 100 includes an encapsulation media 112 which includes a biodegradable polymer and an isolated nucleic acid homolog sequence 110 designed to alleviate symptoms of the medical condition and an encapsulator 114 designed and constructed to encapsulate within nanoparticles 116 the isolated nucleic acid homolog sequence 110 within the encapsulation media 112. System 100 further includes a delivery device 118 designed and constructed to introduce nanoparticles 116 into the subject where isolated nucleic acid homolog sequence 110 is released over an extended period of time.

System 100 and method 200 may thus be advantageously employed in treatment of a medical condition of a subject by sustained delivery of an isolated nucleic acid homolog 110 sequence. In this case, method 200 includes encapsulating an isolated nucleic acid homolog sequence 110 designed to alleviate symptoms of the medical condition within an encapsulation media 112 so that nanoparticles 116 are formed and delivering 218 nanoparticles 116 into the subject where isolated nucleic acid homolog sequence 110 is released over an extended period of time. The medical condition may be, for example, restenosis following balloon angioplasty.

The present invention is further embodied by nanoparticles 116 capable of delivery of an encapsulated molecule into a living cell. Nanoparticles 116 include an encapsulation media 112 that includes a biodegradable polymer as described hereinabove and an isolated nucleic acid homolog sequence 110 encapsulated within encapsulation medium 112. Nanoparticles 116 are capable of releasing isolated nucleic acid homolog sequence 110 over an extended period of time. Sequence 110 is designed to perform at least one function within the cell as detailed hereinabove.

Preferably nanoparticles 116 of the present invention are characterized by an average particle size in the range of 200 to 700 nm. When isolated nucleic acid homolog sequence 110 includes primarily an antisense sequence, particles 116 are more preferably characterized by a particle size in the range of 200 to 400 nm. Alternately, but also more preferably, when isolated nucleic acid homolog sequence 110 includes primarily plasmid DNA, particles 116 are characterized by a particle size in the range of 400 to 700 nm.

The present invention is further embodied by a pharmaceutical composition for treating a medical condition. The composition includes a therapeutically effective amount of nanoparticles 116 capable of delivery of an encapsulated molecule into a living cell. Nanoparticles 116 constitute an active ingredient of the composition. Nanoparticles 116 are essentially as described hereinabove. The composition may further include a physiologically acceptable carrier and/or excipient. Pharmaceutical compositions according to the present invention are expected to find utility in treating medical conditions including, but not limited to cell proliferation disorders, infectious diseases, genetic defects and aberrant gene regulation.

The present invention is further embodied by an article of manufacture including packaging material and a pharmaceutical composition identified for treatment of a medical condition contained within the packaging material. The pharmaceutical composition of the article of manufacture is as described hereinabove.

The nanoparticles of the present invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to isolated nucleic acid homolog sequence 110 accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, sodium carbomethylcellulose; and/or physiologically acceptable polymers such as polyvinylpyrtolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluorometlhane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continues infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (isolated nucleic acid homolog sequence 110) effective to prevent, alleviate or ameliorate symptoms of a disorder (e.g., restenosis) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredient are sufficient to induce or suppress angiogenesis (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

The present invention is further embodied by a method 300 (FIG. 19) of blocking expression of a specific nucleic acid sequence 320. Method 300 includes administering an isolated nucleic acid homolog sequence 110 designed and constructed to specifically hybridize 330 to at least a portion of the specific nucleic acid sequence 320 so that a multistranded complex is formed.

According to some preferred embodiments of method 300, specific nucleic acid sequence 320 is a genomic DNA sequence and the multistranded complex is a triple helix. In this case, isolated nucleic acid homolog sequence 110 may be designed, for example, to hybridize 330 to a transcriptional initiation sequence. Isolated nucleic acid homolog sequence 110 may be, for example is a PNA sequence in order to increase stability of hybridization 330, as detailed hereinabove.

According to alternate preferred embodiments of method 300 specific nucleic acid sequence 320 includes at least a portion of an mRNA transcript (e.g. a sequence including a translation initiation codon or a portion of a 5' untranslated region [UTR]) so that the multistranded complex is a double helix. According to these embodiments, method 300 may further include allowing the multistranded complex to be enzymatically degraded, for example by RNAase H.

Most preferably the isolated nucleic acid homolog sequence 110 is selected from the group consisting of SEQ. ID. NOs. 1-24.

Practice of method 300 may further include sustaining delivery and release of nucleic acid homolog 110 by encapsulating 210 the nucleic acid homolog 110 within nanoparticles 116 and introducing 218 nanoparticles 116 into the subject.

Nucleic acid homolog 110 in the form of SEQ. ID. NOs. 2, 4, 5, 7 and 9 has been experimentally tested against control sequences 1, 3, 6, 8 and 10 as described in example 10, 11 and 12 hereinbelow. Owing to the high degree of functional similarity between the rat, mouse and human PDGFβR genes, results presented in these examples are deemed experimental proof of the utility of SEQ. ID. NOs. 11, 13, 15, 17, 19, 21 and 23 compared to SEQ ID NOs. 12, 14, 16, 18, 20, 22 and 24 in the context of the present invention.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology". Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York, Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiugi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hanies, B. D., and Higgins S. J., eds. (1985); "Transcription and Translation" Haines, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Specific reference is also made to the following methods and materials, which are employed in conducting experiments described in the following examples.

Methods and Materials

Reagents: Poly(DL-lactide-co-glycolide) polymer (PLGA) of a lactide-glycolide ratio of 50:50, inherent viscosity of 1.13 dl/g, and MW of 123 400 was obtained from Birmingham Polymers (Birmingham, Ala., USA). Polyvinyl alcohol (PVA) at average MW range of 15,000-30,000, thiazole orange, agarose, ethidium bromide, and 3-[(3-cholamidopropyl)-dimethylammonio]-1-1propanesulfonate (CHAPS) were obtained from Sigma Chemical Co. (St Louis, Mo., USA). TOTO-1 (dimeric cyanine nucleic acid stain) was obtained from Molecular Probes (Eugene, Oreg., USA). Lipofectamine (GibcoBRL, Gaithersburg, Md., USA), and Escort (Sigma) are similar liposome formulations of cationic (DOSPA or DOTAP) and neutral lipids (DOPE) at a ratio of 1:1 (both termed as LIP). Lipofectamine and Escort were used in the in vitro and in vivo transfection experiments, respectively. Optimal cutting temperature compound (OCT) was obtained from BDH Laboratory Supplies (Poole, UK). All other chemicals were obtained commercially at the highest analytical grade available. All buffers and solutions were filtered through 0.2 mm filters for sterilization.

ODN sequences: Oligodeoxynucleotides were either synthesized in house by automatic synthesizer (PerSeptive Biosystems, Multiple Oligo Synthesis System, GEN600173, MOSS) or ordered from a commercial suppliers (Alpha DNA, Montreal, Quebec, Canada). Analytical, semi-preparative and preparative HPLC and Electrospray ionization mass spectrometry (ESI-MS), and MALDI-TOF analyses were employed to verify homogeneity of prepared ODNs. The solid phase oligomerizations, purification and characterization of PNAs were performed in house using either the commercially available monomers (PE-Biosystems) or which have been synthesized. PNA oligomerization was done either manually or using an Automatic Synthesizer (ChemSpeed, ASW2000). The following ODNs were synthesized:

| SEQ ID NO | name | length | sequence | | Used in examples |
|---|---|---|---|---|---|
| 1 | SC (II) | 18 | CGGAGAGAGGCCGTCGAT | PartialPT | 10&12 |
| 2 | AS (II) | 18 | CGGGAGGAAGCCCATGGT | PartialPT | 10&12 |
| 3 | SC-S (II-S) | 18 | CGGAGAGAGGCCGTCGAT | PT | 10 |
| 4 | AS-S (II-S) | 18 | CGGGAGGAAGCCCATGGT | PT | 10 |
| 5 | R-AS-PT-ODN (III) | 18 | TATCACTCCTGGAAGCCC | PartialPT | 10 |
| 6 | R-SC-PT-ODN (III) | 18 | TTACACTCCTGGACAGCC | PartialPT | 10 |
| 7 | H-AS-PT-ODN | 18 | GAGCACAGGCTCGTGCTG | PartialPT | 11 |
| 8 | H-SC-PT-ODN | 18 | GAGGTGGAGCTCCACCTG | PartialPT | 11 |
| 9 | H-AS-PT-ODN | 18 | CGGAAGCCGCATGGTGTC | PartialPT | 11 |
| 10 | H-SC-PT-ODN | 18 | CGGGTGCCGCATGAAGTC | PartialPT | 11 |
| 11 | H-AS-PT-ODN | 18 | AGAGCTGGCATCGCACC | PartialPT | |
| 12 | H-SC-PT-ODN | 18 | AGCGATGGCATCGCACCC | PartialPT | |
| 13 | H-AS-PT-ODN | 18 | ATTTAAGCATCTTGACGG | PartialPT | |
| 14 | H-SC-PT-ODN | 18 | ATAATTGCATCTGGTGAC | PartialPT | |
| 15 | M-AS-PT-ODN | 18 | TGATTGCGGAAAACCCTG | PartialPT | |
| 16 | M-SC-PT-ODN | 18 | TTGTAGCGGCACAACATG | PartialPT | |
| 17 | M-AS-PT-ODN | 18 | TGGAAGCCCCATGGTGTC | PartialPT | |
| 18 | M-SC-PT-ODN | 18 | GGATAGCCCCATGTGTGC | PartialPT | |
| 19 | M-AS-PT-ODN | 18 | AGGAAGCCCATGGTGGGA | PartialPT | |
| 20 | M-SC-PT-ODN | 18 | GAAGAGCCGAGTCTGGGA | PartialPT | |
| 21 | R-AS-PT-ODN | 18 | TGGAAGCCCCATGGTGCC | PartialPT | |
| 22 | R-SC-PT-ODN | 18 | TGGAAGACTCGCGGTCCC | PartialPT | |
| 23 | R-AS-PT-ODN | 18 | TCCTCGCTGTCCTGTTAT | PartialPT | |
| 24 | R-SC-PT-ODN | 18 | TTCCCGCTGCTCGTTTAT | PartialPT | |
| 25 | Navig peptide | 25 | Ser-Val-Lys-Ala-Gln-Trp-Lys-Lys-Asn-Lys-His-Arg-His-Gly-Cys-Gly-Arg-Leu-Thr-Arg-Lys-Arg-Gly-Leu-Lys | | |

Partial PT refers to partial thioation of the phosphodiester backbone at 5'- and 3' tremini of the sequence. PT refers to thioation of all phosphodiester backbone throughout the sequence.

Plasmid DNA Preparation: The human placental alkaline phosphatase (AP) gene (1.9 kbp) was cloned in pcDNA3 vector (5.4 kbp; Invitrogen, San Diego, Calif., USA) forming AP/pcDNA3 reporter plasmid (7.3 kbp). The plasmid was amplified in E. coli host strain, DH5α extracted by the alkaline lysis technique, and purified using plasmid Giga column isolation kit (Qiagen, Hilden, Germany). Plasmid DNA concentration measurements were based on absorbancy at 260 nm, and on fluorescence assay using thiazole orange as an intercalated dye, with excitation at 500 nm and emission at 530 nm.

NP preparation and characterization: A double emulsion system and the solvent evaporation technique were used to incorporate the pDNA in PLGA. Briefly, 200 µl of Tris-EDTA (TE) buffer (0.1 mm Tris and 10 mm EDTA) containing 500-1000 µg of pDNA (initial loading of 0.55-1.1 w/w%) were emulsified in 3% PLGA/chloroform solution (3 ml) using a homogenizer (Omni TH, Omni International, Warrenton, Va., USA) at 30,000 r.p.m. for 1.5 min. The resulting primary emulsion was added dropwise to a 2% PVA solution (in 25 ml TE), and homogenized for 4 min, forming the double emulsion. Following overnight evaporation at 4° C., the formed particles were collected by ultracentrifugation at 80,000 g (TST28 rotor, Beckman's polyallomer centrifuge tubes, 25×89 mm), washed three times with sterile DDW, resuspended in double distilled sterile water, and lyophilized. In some experiments, calcium chloride from a stock solution of 2.5 m was added to the PVA phase (Table 1, row 2). Several formulations were prepared in order to study the effect of initial loading (Table 1, row 1) and calcium/pDNA ratio (Table 1, row 2) on encapsulation efficiency and bioactivity. The amount of pDNA entrapped in the NP (PDNA final loading) was analyzed by dissolving the NP (10 mg) in chloroform (1.5 ml), and the pDNA was extracted from the polymer solution by repetitive additions of TE buffer (×5, 0.5 ml). pDNA content and integrity were determined as described above.

TABLE 1

Features of pDNA-NP preparation

| FORMULATION | NPO (n = 2) | NP1 (n = 5) | NP2 (n = 5) | NP3 (n = 5) |
|---|---|---|---|---|
| Initial pDNA conc. (w/w %) | 0.55 | 0.55 | 1.10 | 0.55 |
| Ca in PVA phase (mg % w/v) | 0.0 | 12.4 | 24.8 | 24.8 |
| DNA in Exterior Phase (% of initial) | 31.9 ± 3.6 | 9.7 ± 5.3 | 8.8 ± 4.7 | 8.8 ± 4.9 |
| DNA entrapped (% of initial) | 27.9 ± 1.0 | 73.8 ± 21.3 | 67.5 ± 13.4 | 69.3 ± 15.5 |
| DNA Final loading (% w/v) | 0.15 | 0.41 | 0.74 | 0.38 |
| Ca in exterior phase (% of control formulation) | — | 101.4 ± 11.4 | 97.1 ± 6.2 | 99.4 ± 5.8 |
| Particle size (nm) | 589.0 ± 190 | 643.5 ± 74.1 | 639.9 ± 63.9 | 537.5 ± 108.6 |
| Zeta potential (Δmv) | 0.0 | 7.4 ± 3.3 | 9.3 ± 6.8 | 10.8 ± 5.0 |

Size, morphology, z-potential and pDNA distribution in the NP: Laser light scattering (Coulter N4 submicron particle size analyzer, Luton, UK), scanning electron microscope and transmission electron microscope (SEM 505 and TEM CN12, respectively; Philips, Eindhoven, The Netherlands) were used to determine particle size, size distribution, and morphology. For laser light scattering, the particles were suspended in sterile DDW, the sample intensity (level of cloudiness) was between $5 \times 10^4$ to $1 \times 10^6$ counts per second, and the average number is given. The zeta potential was measured by means of a Zetamaster device (ZEM, Malvern Instruments, Orsay, France) using a rectangular quartz capillary cell. The particles' concentration was about 1 mg per 3 ml sterile DDW and diluted if necessary according to the instrument's cloudiness requirements. pDNA in the NP was fluorescent-labeled after encapsulation by intercalation with ethidium bromide. Both blank and pDNA-NP (5 mg) were incubated for 3 h in ethidium bromide solution (1 μg/1 ml), centrifuged, washed (×3), resuspended in sterile dd water, and examined by microscope. A confocal fluorescence laser scanning microscope was used to detect pDNA in the NP (Axiovert 135M, Ziess 410, Germany; filter set at 488/605).

Fluorescent (FITC) labeled PT-ODNs and PNA were encapsulated in PLGA. A confocal fluorescence laser scanning microscope was used to detect the PT-ODN and the PNA in the NPs (Axiovert 135M, Zeiss 410, Germany; filter set at 488/512).

In vitro release: Plasmid DNA NP (5-20 mg) or PT-ODN were suspended in TE buffer (1 ml). PNA-NP were suspended in a similar volume of dd sterile water. NP suspensions were incubated at 37° C. on a shaker at 100 r.p.m. (Lab Line Instruments, Melrose Park, Ill., USA). At different time-points, the buffer was separated from the NP by centrifugation and analyzed for the amount and integrity of released genetic material. At each time-point, the NP were resuspended in fresh releasing medium. The release rate of entrapped pDNA was studied in comparison with a suspension of blank NP with added pDNA, PVA and calcium in amounts used in the preparation of pDNA-NP.

Gel electrophoresis: pDNA either released or extracted from the NP was analyzed by gel electrophoresis for purity and structural integrity before and after enzymatic digestion (1% agarose, 0.1 mg % ethidium bromide in 1× TBE buffer, 100 V, 45 min). The marker λHindIII (Sigma) and the restriction enzyme pstI/buffer H (GibcoBRL) were used for the gel analysis. pDNA released (at several time-points, from 1 day to 1 week) or extracted (the extraction method is described under NP preparation), was combined in one tube, precipitated with Et-OH, resuspended in TE buffer, and examined by gel electrophoresis. The bioactivity of released and extracted pDNA was investigated in comparison with an unencapsulated plasmid by in vitro transfection of NIH 3T3 cells, using a standard calcium phosphate (CaPi) mediated cell transfection protocol (Yang and Yang (1996). Drug Del 3: 181-186). and 1.5 μg pDNA. For released pDNA, a volume of the supernatant containing the same amount of pDNA was directly taken for transfection. Extracted pDNA was precipitated with Et-OH, resuspended in TE buffer, and examined for transfection. Cells were plated at a density of $1 \times 10^5$ cells per 35 mm well (six-well plate) and incubated for 24 h before transfection. Cells were lysed with 250 μl of TMNC buffer (50 mm Tris, 100 mm NaCl, 5 mm $MgCl_2$, and 4% CHAPS) 48 h after transfection, and the lysed cell supernatant was heated at 65° C. for 30 min in order to inactivate endogenous AP (the recombinant AP is stable at these conditions). A specific chemiluminescence assay kit (Tropix, Bedford, Mass., USA) was used to determine the recombinant AP levels by means of a luminometer (Turner Designs 2020, Sunnyvale, Calif., USA). An aliquot of 20 μl lysate, and 20-min incubation time were used in the assay. The average luminescence reading of the negative control group (cells only) was determined as background and was subtracted from the readings of the other experimental groups. Results were normalized to total protein content determined by BCA total protein assay (Pierce, Rockford, Ill., USA), and are expressed as light units (LU) per milligram protein.

Cell culture studies: NIH 3T3 mouse fibroblasts and 293 human endothelial cell lines were cultured in DMEM (high glucose), 10% fetal calf serum, 2 mm glutamine, and penicillin-streptomycin (100 U/ml and 0.1 mg/ml, respectively; Biological Industries, Beit Haemek, Israel). Cells were maintained at 37° C. in an incubator, at a 5% $CO_2$ humidified atmosphere.

Reagents used for culturing Rat Smooth Muscle Cells (SMC) and ZnR5 cells were obtained from Biological Industries, Beit Haemek, Israel, unless otherwise noted. SMCs were isolated and cultured from thoracic aortas of Sabra male rats weighing 200-300 g by the explant method (Fishbein et al. (2000) Thromb Vasc Biol 20:667-76). Freshly dissected blood vessels from animals killed less than 5 min. previously were placed in cold media. The vessels were aseptically cleaned by removing the fat and connective tissue (adventitia) and were cut longitudinally. The lumen side was gently scraped with a scalpel blade to dislodge endothelial cells. The vessel wall was then cut with a scalpel blade into 2 mm$^2$ explants and the luminal surface gently pressed on fibronectin coated surface (3 μg/cm2) of 24-multiwell dishes. Fibronectin was used to promote cell adhesion as suggested previously (Weinstein et al. pp. 145-154 and Yamad et al. pp. 131-143 In: Sato et al. eds. *Growth of cells in hormonally defined media*. (1982) Cold Spring Harbor: Cold Spring Harbor Laboratory).

Explants were left to adhere undisturbed for 1 hr. and growth media was added. Rat aortic explants were cultured in 15% fetal calf serum (FCS) in DMEM high glucose (4500 mg/l) with penicillin (100 U/ml), streptomycin (0.1 mg/ml), and glutamine (2 mM) supplements in a humidifier incubator at 37° C. and 5% $CO_2$ atmosphere. Explants were left undisturbed for the first week, and media was changed every two days from the second week. When the cells growing from the explants reached confluency, explants were aspired and cells were subcultured with 0.25% trypsin and placed in 10 ml dishes with the medium changed every two days. The cells beyond the first passage were replated on 24-well plates pre-treated with fibronectin at 15000 cells/well and cultured in DMEM, 10% FCS, 1% glutamine, 100 U/mL penicillin, and 100 □g/mL streptomycin. Cells were used from the first through the fifth passage. Cell identity was confirmed through microscopic observation (characteristic "hill and valley" growth pattern), and smooth muscle α-actin immunocytochemistry (Sigma).

ZnR5 cells that express human PDGFRβ were maintained as described above for SMC.

Visualization of cellular uptake: The PLGA used in this study was labeled with pyrene (Py) by esterification of the hydroxyl group of the polymer with 4-(1-pyrene)butyryl chloride as described previously (Slomkowski (1989) *Macromolecules* 22: 503-509) forming fluorescent pyrene-PLGA. Blank-NP were prepared with the labeled polymer in order to study their uptake by cells. Cells (1×10$^4$ per chamber) were seeded on a Lab-Tek chambered cover glass system (Nalge Nunc, Naperville, Ill., USA) and incubated for 24 h before transfection. The NP were suspended in the cell media (3 mg/0.4 ml) and added to the cells at NP to media volume ratio of 1/10 (300 μg NP). Following incubation for 5 h, cells were carefully washed with PBS (×3), fixed with absolute methanol for 4 min, washed (×3) with PBS, and mounted with fluorescence microscopy mounting media (Sigma). Pyrene-PLGA NP localization was detected by confocal fluorescence microscopy using a UV excitation laser with appropriate filter sets. Encapsulated PDNA was labeled with the cell impermeable DNA fluorescence probe TOTO-1 (Molecular Probes), in order to examine its cellular uptake and localization. Blank-NP (3 mg), pDNA containing NP, and a corresponding amount of naked pDNA were incubated for 0.5 h with a solution of TOTO-1 (600 μl, 1 mm). NP were then centrifuged, washed (×3) to remove probe access, and suspended with cell media. Transfection and fixation of cells were carried out as described above.

In vitro transfection: AP expression was determined following direct transfection of 293 human endothelial cells by pDNA-NP (2 μg pDNA) examining the effect of the following variables: addition of LIP (12 μl of 2 mg/ml solution), lysosomotropic agent, chloroquine (100 mm; Hedin and Thyberg (1985). *Eur J Cell Biol* 39: 130-135), and an osmotic swelling agent, sucrose (88 mm; Kato et al. (1984) *Mol Cell Biochem* 60:83-98). Transfection was examined after 48 h and 1 week in order to evaluate the bioactivity of sustained release pDNA (bursteffect of release was observed up to 24 h). The overall expression levels in the cells+pDNA group are expected to be very low, and either to remain the same or to decrease from 48 h to 1 week (cells number increase, and results are normalized to total protein). Transfections with the liposomal formulation, LIP, served as positive control groups (named as pDNA-LIP). Since the transfection of pDNA released after 48 h could be enhanced by LIP, experimental group of cells+pDNA-NP+LIP was examined. The latter two groups were subdivided into two additional groups in which LIP, or LIP and 2 mg of pDNA, were also added at 48 h. The second addition of LIP to the NP's group was carried out to see if the bioactivity of pDNA released at later time-points could be enhanced. The second addition of pDNA to the cells+pDNA and cells+pDNA-LIP groups served for comparison With the bioactivity of pDNA released at later time-points. Cells were plated in 35 mm plate in 3 ml full media (as above). Transfection experiments with the pDNA-LIP groups were performed according to the manufacturer's instructions. Briefly, 12 μl of LIP and 2 μg pDNA/2 μl, both in 100 μl of serum-free media, were combined. The 200 μl solution was incubated for 20 min, 0.8 ml full media was added, and the solution was added to the cell culture plates after removing their media. The media containing LIP was replaced after 5-6 h and 1 day with fresh media. In the pDNA-NP group, 12 μl of LIP was added dropwise to the NPs containing media. After 48 h, cells and media (in the NP groups, with the NP) were removed to a 10 cm dish, fresh media was added to a final volume of 10 ml, and the plates were incubated until the 1 week timepoint. In the experimental groups of second LIP addition, LIP (12 μl) was added dropwise at 58 h. All groups were incubated to confluency (1 week), AP levels were determined, and the reported results were normalized to total protein content. The possible deleterious effects of polymeric particles on transfection and expression capabilities were studied by measurement of AP (2 mg of naked pDNA) expression following CaPi transfection of 293 and NIH 3T3 cell lines in the presence of blank NP. Cells were plated at a density of 1' 105 cells per 35 mm plate and incubated for 24 h before transfection. Blank NP (1 mg) were suspended in the cell medium and added to the cells 6 h before or after the CaPi procedure was conducted. Cells were carefully washed free of particles (×3) in the pre-transfected group. In the control group, media was changed after 24 h. AP levels were determined 48 h after transfection.

Inhibition of smooth muscle cells (SMCs) proliferation: SMCs were explanted from rat artery and cultured as described above. For proliferation assay, cells were seeded in 24-well plates at a density of 15000 cells per well (15000/mL) at day 0. At day 1, the original medium was replaced with a growth arrest medium (DMEM containing 0.1% FCS) in order to bring all the cells to the S1 stage. At day 4, the arrest medium was replaced with full medium (15% FCS) containing naked AS sequences, blank NP, SC-NP, or AS-NP, at various concentrations. Control wells received only medium. At day 7 cells were washed with PBS buffer, SMC were released from the plate by trypsinization, and cell number was determined by means of a coulter counter. Experimental groups were done in triplicate. Percent inhibition was calculated as [1-(average cell number in treated wells/average cell number in control wells)]*100.

Inhibition of ZnR5 cells (express human PDGFβ) proliferation: Cells were seeded in 96-well plate (2000 cells per well). The original medium was replaced with growth arrest medium (0% FCS) and the cells were serum starved for 48 hrs.

Cells were then stimulated with PDGF-BB (1 ng/ml) and transfected with various concentration (5, 10, 15 and 20 μM) of ATG and UTR antisense and scrambled sequences. Following incubation overnight the proliferation was quantified using BrdU Kit (Roche, Postfach, Switzerland).

Inhibition of neointimal formation—Rat injured carotid model: The AS-NP were tested in-vivo in previously described experimental model for restenosis (Chorny et al. (2000). Crit. Rev. Ther. Drug. Carrier. Syst. 17:249-84 and Golomb et al. (1996) Atherosclerosis. 125:171-182). The procedures were adapted Fishbein et al. (2000) Arterioscler Thromb Vasc Biol. 20:667-76; Fishbein et al. (2000) J. Controlled Release. 65:221-9 and Fishbein et al. pp 313-335. In: Wise D L, ed. Biomaterials and bioengineering handbook. New York: Marcel Dekker, Inc; 2000) with some modifications and adjustment for antisense delivery. Animals were obtained from Harlan Laboratories, Israel, and housed in the animal facilities of the Faculty of Medicine, The Hebrew University of Jerusalem, Jerusalem in conformation with the standards for care and use of laboratory animals of The Hebrew University of Jerusalem and The NIH. The animals were fed standard laboratory chow and tap water ad libitum. All in-vivo experiments were conducted under general anesthesia achieved with 80 mg/kg ketamine and 5 mg/kg xylazine (i.p.).

The distal left common and external carotid arteries of male Sabra rats (350-420 g) were exposed through a midline incision in the neck. The left common carotid artery was denuded of endothelium by the intraluminal passage of a 2F balloon catheter (Baxter Healthcare Corp., Calif., USA) introduced through the external carotid artery. The catheter was passed three times with the balloon distended sufficiently with saline to generate a slight resistance. For intraluminal delivery, 50 units of heparin (in 0.2 ml saline) were injected through the tail vain before the balloon injury. A 2 cm piece of the 10 PE polyethylene tubing was mounted on the 23G hypodermic needle. A 1 ml syringe containing AS solution was connected to the needle, and the dead space of the needle and tubing was completely filled. After Fogarty catheter withdrawal the tip of the tubing was inserted through the preformed orifice in the external carotid artery and advanced an additional 4-5 mm into the common carotid artery. To enable an adequate fixation of the tubing and assure hermetization of the arterial segment an additional suture was placed at the origin of the cannulated common carotid artery immediately near the bifurcation. The isolated arterial segment was then bathed with ca. 50 μl naked SC (20 mM/50 μl saline, 1 nmole) or naked AS solutions, or with suspensions of blank NPs, SC-NP and AS-NPs (similar amount of the naked sequence) during a period of 20 minutes. The syringe and the tubing were then withdrawn, and the external carotid artery was tied off proximally to the site of the tubing entry. This 'bathing method' mimics to some extent the envisaged clinical applications employing 'sweating/oozing balloons' or coated stents.

All animals were sacrificed 14 days after injury by an overdose of ether. Arteries were perfusion-fixed with 150 ml of 4% formaldehyde solution pH 7.4 at 100 mm Hg. The right atrium was dissected and an 18G catheter connected to the perfusion system was inserted in the left ventricle. The arterial segments were dissected, cut, gently separated from the polymer, and postfixed for at least 48 hrs. in the same fixative solution. The central part of the arterial section was taken for histologic examination. The arterial segments were embedded in paraffin and cut at 8-10 sites 600 μm apart, and sections of 6 μm were mounted and stained with Verhoeff's elastin stain.

Morphometric analysis: Two types of slide evaluation were employed. In the first type of evaluation, every slide was studied microscopically by an investigator blinded to the origin of the slide. A single section in every slide was chosen by the blinded investigator as being the section having the maximal degree of neointimal formation. Then a computerized morphometric analysis of the chosen section was performed using a dedicated imaging system (Olympus BX40 microscope equipped with the Sony 3 CCD video camera and interfaced with a Power Macintosh computer running Scion Image 1.62 software).

The second type of evaluation was based on morphometric analysis of all sections in the slide (typically 8 to 10). The directly measured values, as well as calculated indices were then averaged for all assessed sections in the slide. The latter method provides a more accurate estimation of the vessel obstruction since it takes into account the degree of the arterial patency at several sites along the injured segment. The former approach has the advantage of better clinical relevancy since in human restenosis eventual blood flow through the diseased coronary artery is determined by the status of the most occluded "bottle neck" site. Generally, morphometric results obtained by both methods of calculation correlated well and both are reported. The presented results in this work were calculated from the maximal degree of neointimal formation slide section of each artery.

The residual lumen, the area bounded by the internal elastic lumina (original lumen), and the area circumscribed by the external elastic lamina ("total arterial area") were measured directly. The degree of neointimal thickening was expressed as the ratio between the area of the neointima and the original lumen (percent stenosis) and as the ratio between the neointimal area to the area of the media. The medial area, an indirect index of SMC viability, was determined as the difference between the total arterial area and the original luminal area.

In vivo transfection: Six-week-old Sprague-Dawley male rats (The Hebrew University of Jerusalem, Jerusalem, Israel) were anesthetized by ether and randomly assigned. The tibial area was shaved and saline (100 ml) was longitudinally injected in the muscle using a 1 ml sterile syringe fitted with a 25 G ⅝ needle (Microlance, Becton Dickinson, Fraga, Spain) as described previously (Levy (1996) Gene Therapy 3: 201-211). PDNA (25 μg pDNA/200 μl saline), pDNA-LIP (containing 25 μg pDNA) or pDNANP suspension (containing 25 μg pDNA) were injected 10 min later in the same procedure. The control group received either saline or blank-NP. Three, seven and twenty eight days after pDNA administration, the tibial muscle was harvested, homogenized, and incubated for 15 min with 1 ml TMNC buffer, and AP and protein concentrations in the lysate were determined as above. Several specimens of transfected muscles (at least from two rats) were randomly excised from the control and experimental animal groups. The muscles were cut to small pieces, embedded in OCT compound and frozen at −70° C. Eight micron cross-sections were prepared using a cryostat (Cryostat CA3000, Leica Microsystems, Nu'loch, Germany). Ten randomly selected frozen sections from each group were washed with PBS, heated at 65° C. for 30 min, immersed 30 s in citrate-acetone-formaldehyde fixative solution (volume ratio of 25:65:8, respectively), and incubated for 15 min with FRV-alkaline dye mixture for AP cytochemistry (Sigma). The slides were rinsed, counterstained with hematoxylin solution (Gill No. 3, Sigma), and coverslipped by aqueous mounting media.

Data analysis: Results were expressed as mean□SEM. Statistical differences between groups in the in-vitro experiments were assessed by the Kruskal-Wallis nonparametric test, using the InStat software package (GraphPad Software Inc., San Diego, Calif.). When required, this test was followed by the Dunn's multiple comparisons post hoc test (p<0.05 was termed significant). Differences between AS to SC groups in the experiment assessing antirestenotic activity were termed significant by the unpaired Student t test at p<0.05, using the InStat software.

Example 1

Comparative Formulation of PLGA-pDNA

In order to determine an optimum formulation for PLGA-pDNA nanospheres, various calcium concentrations and calcium to pDNA ratios were employed. Results of physico-chemical characterization of the formulations are summarized in Table 1 (presented hereinabove). The addition of calcium to the exterior phase (formulations NP1-NP3) resulted in a high encapsulation efficiency of about 70% in comparison with only 28% in the absence of calcium (NP0). Increasing the initial concentration by two-fold, or increasing the calcium/DNA ratio by two-fold resulted in insignificant changes in the final loading of pDNA in the NP. pDNA in exterior and pDNA entrapped (Table 1, rows 3 and 4) do not sum to 100% since some pDNA was apparently lost in the interphase between chloroform and aqueous phase during extraction. Reduction of 33% in calcium concentration was found in the exterior phase. However, the same reduction in calcium concentration was found in both pDNA formulations and in their corresponding controls (i.e. particles with a similar amount of calcium but without pDNA) indicating that this loss is a function of the extraction process.

Figure 2C:
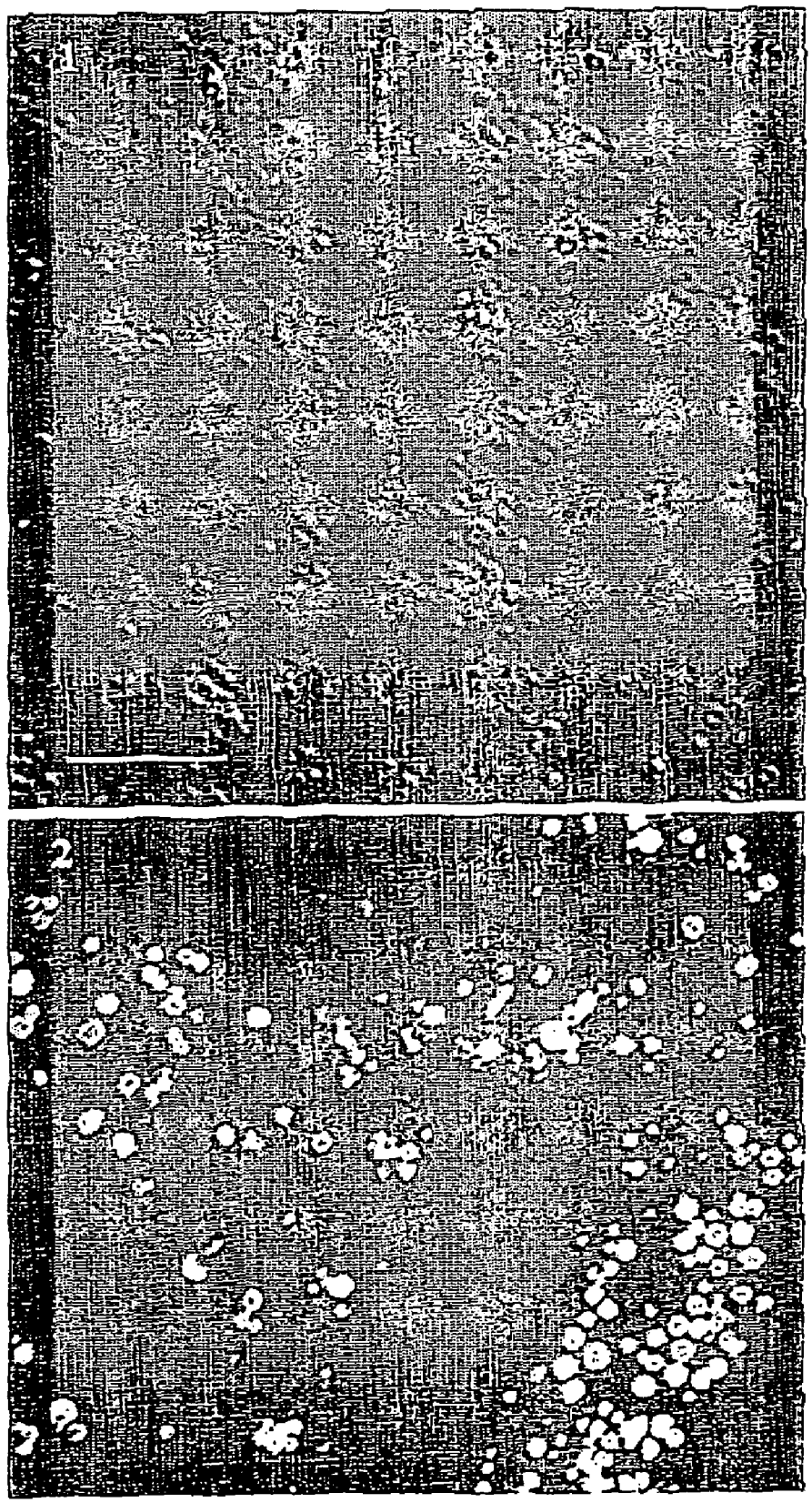

Following pDNA entrapment, the z-potential of the PLGA particles decreased by 7-10 mV. The pDNA loaded PLGA particles were found to be in the nano range with a spherical shape (see FIGS. 2a and 2b). Post-labeling of pDNA-NP with the DNA fluorescence probe, Et-Br, showed a fluorescence signal in over 80% of the particles (FIG. 2c). Confocal fluorescence microscopy of cross-sectioned particles revealed pDNA distributed within the particles. The actual size of the NP is apparently higher than that measured by the Coulter Counter (Table 1), a known fluorescence-related artifact. The release rate of entrapped pDNA was measured and compared to a suspension of blank-NP supplemented with pDNA (FIG. 3). For the latter it was found that 103.0±1.5% of the pDNA added was recovered after 24 h, indicating no adsorption of pDNA on the NP. The pDNA sustained release profile from the various pDNA-NP formulations (Table 1) was similar over 1 month, with a burst effect of about 50% release after 1 day. These results indicate that the tested nanoparticle formulations are capable of providing sustained release of ODNs.

Example 2

Analysis of Structural and Functional Integrity of pDNA Encapsulated in PLGA nanoparticles Plasmid DNA Encapsulated in PLGA NP retained its structural integrity following enzymatic digestion and exhibited a pattern similar to intact pDNA (FIG. 4b). However, the ratio between relaxed (nicked) to supercoiled conformation of encapsulated pDNA in comparison with control pDNA increased from 30:70 to 60:40% (FIG. 4a). pDNA either released or extracted from the various formulations (Table 1; presented hereinabove) had a similar relaxed/supercoiled pattern, and was found to be bioactive as indicated by its transfection efficiency in NIH 3T3 cells (Table 2). The decreased proportion of supercoiled DNA was loosely correlated to lower expression levels but the difference was statistically insignificant. AP expression level of naked pDNA was $17.1 \times 10^5 \pm 10.4 \times 10^5$. No statistical difference was found between the various groups. These results indicate that that the additional nicking of the plasmid DNA as a result of encapsulation did not adversely affect transfection efficiency or subsequent expression after transfection. Thus, nanoparticles according to the present invention seem well suited for use in cellular delivery of ODNs.

TABLE 2

Functional integrity of pDNA encapsulated in nanoparticles (NP). Alkaline phosphatase expression levels in LU/mg protein after 48 h (1.5 µg pDNA, mean ± s.e.m., n = 4)

| formulation | pDNA extracted from NP[a] | pDNA released from NP[b] | |
| --- | --- | --- | --- |
| | | 5 hours | 1 day |
| NP1 | $8.4 \times 10^5 \pm 2.52 \times 10^5$ | $1.1 \times 10^5 \pm 1.4 \times 10^3$ | $2.7 \times 10^5 \pm 3.5 \times 10^4$ |
| NP2 | $23.9 \times 10^5 \pm 3.84 \times 10^5$ | $2.4 \times 10^5 \pm 2.0 \times 10^4$ | $1.3 \times 10^5 \pm 3.7 \times 10^3$ |
| NP3 | $25.2 \times 10^5 \pm 1.22 \times 10^6$ | $3.4 \times 10^5 \pm 8.5 \times 10^4$ | $4.5 \times 10^5 \pm 7.0 \times 10^4$ |

[a]The full content of pDNA in the NP was extracted (see *Materials and methods*).
[b]pDNA was released from the NP in buffer (see *Materials and methods*).

Example 3

Cellular Incorporation of ODN Encapsulated in PLGA Nanoparticles

Figure 5A:
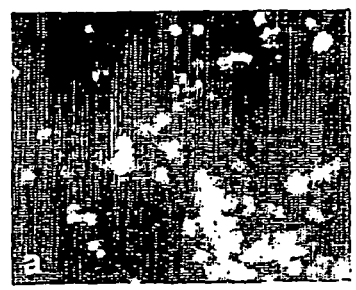
FIGS. 5a and 5b are Confocal images of NIH 3T3 cells transfected with fluorescent blank-NP For FIG. 5a, PLGA was labeled with the fluorescent probe, pyrene, before NP preparation. Confocal cross-sections presented in FIG. 5b verified cell internalization (green-blue colors) or NP on cells' surface (red). Spherical NP is subject to perinuclear localization.
Figure 5B:
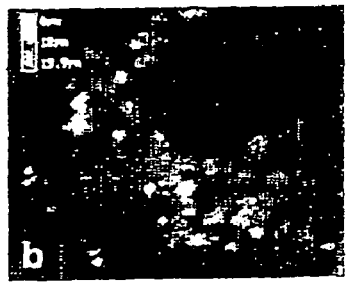
Figure 6A:
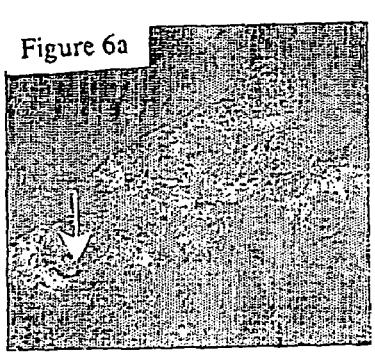
Figure 6B:
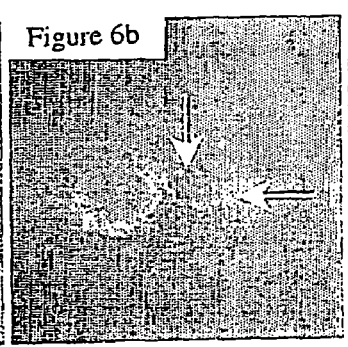
Figure 6C:
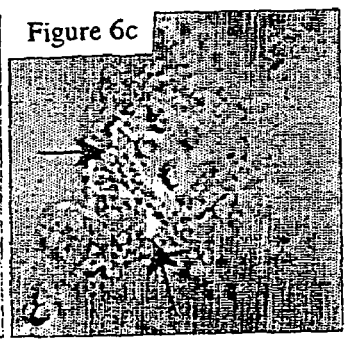

In light of the results described in example 2, an examination of the cellular localization of nanoparticles within cells was conducted. Empty nanoparticles prepared from pyrene-PLGA polymer were incorporated into cells and accumulated in the cytoplasm of transfected NIH 3T3 cells (FIG. 5). In order to examine the cellular uptake of pDNA-NP, encapsulated pDNA was labeled with the fluorescent probe, TOTO-1. This cell-impermeable fluorescent probe exhibits large fluorescence enhancement (1400-fold) upon binding to pDNA. Both blank-NP and naked plasmid exhibited very low fluorescence, determined as background for further analyses. In contrast, both pDNA-NP and released pDNA were detected inside the cells (FIG. 6a-c). pDNA-NP were concentrated mainly in the cytoplasm (FIGS. 6a and c). In contrast, released pDNA (morphology resembling a nanosphere is not observed) was detected in the cytoplasm (FIG. 6a), around the nucleus (FIG. 6b), and to a lesser extent in the nucleus (FIGS. 6a and b). The pDNA detected inside the cell could result only from pDNA that was released intracellularly following internalization of nanoparticles containing pDNA since TOTO-1 labeled DNA is cell impermeable. These results indicate that the tested nanoparticles are capable of releasing plasmid DNA after incorporation into cells, confirming results presented in example 2. Further, these results indicate that nanoparticles according to the present invention can serve as an intracellular delivery reagent for molecules which do not normally penetrate the cell membrane.

Example 4

Transfection of Cultured Cells with pDNA Encapsulated in PLGA Nanoparticles

Figure 7:
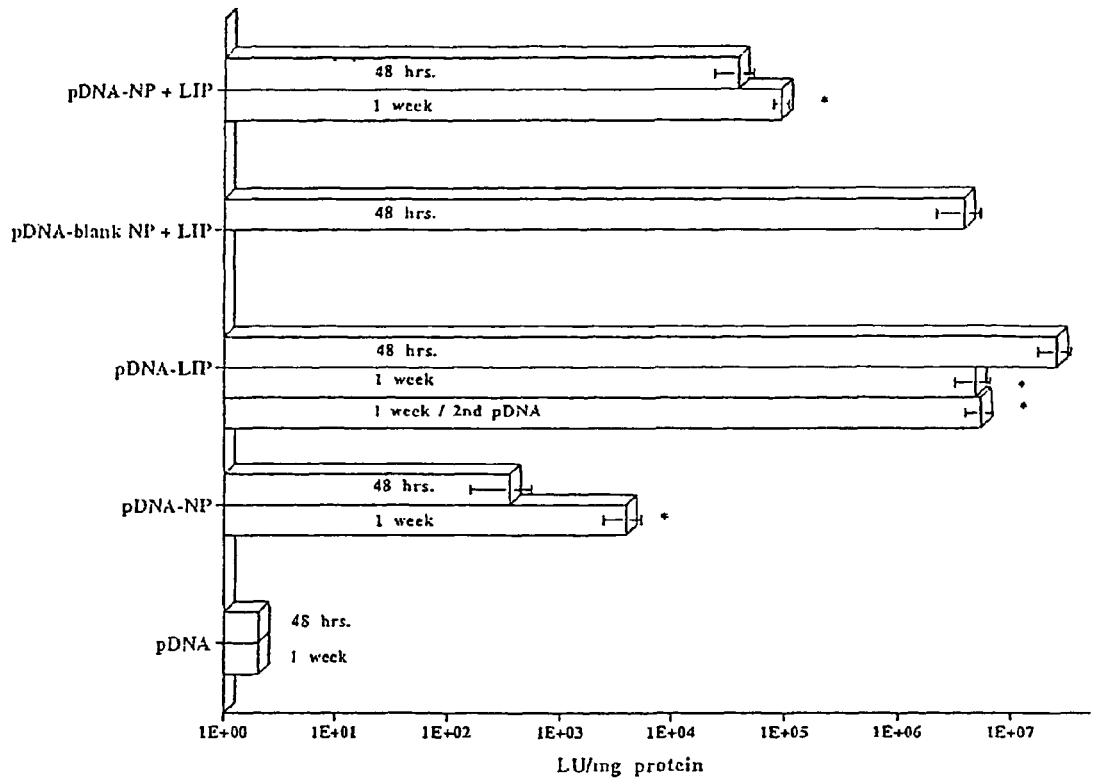
FIG. 7 is a bar graph illustrating Alkaline phosphatase expression following transfection of 293 human endothelial cell lines with pDNA-NP (formulation NP2 was chosen for its high loading, 2 μg DNA, 12 μl LIP, mean±s.e.m., n=4, *P, 0.05). Expression was examined after 48 h and 1 week, with or without the addition of liposomes (LIP).

Expression levels of an alkaline phosphatase reporter gene in 293 cells following transfection with pDNA-NP are summarized in FIG. 7. The various formulations (see Table 1) had similar effects (data not shown). In comparison with naked pDNA, the delivery of pDNA by NP resulted in significantly higher expression levels ($2 \times 10^1 \times 0 \times 10^1$ and $4 \times 10^2 \pm 2 \times 10^2$ LU/ng protein, respectively). pDNA+ addition of pDNA at 1 week, resulted in luminescence levels similar to the cells-only group. In the pDNA-NP group, the AP levels were increased by 10-fold when the transfection time was extended from 48 h to 1 week, ($4 \times 10^2 \pm 2 \times 10^2$ and $4 \times 10^4 \pm 1 \times 10^3$ LU/mg protein, respectively). However, in comparison with the pDNA-LIP group, the expression levels were significantly lower at both 48 h and 1 week ($4 \times 10^2 \pm 2 \times 10^2$ verses $2 \times 10^7 \pm 1 \times 10^7$ and $4 \times 10^4 \pm 1 \times 10^3$ versus $5 \times 10^6 \pm 2 \times 10^6$ LU/mg protein, respectively). The addition of LIP to pDNA-NP increased the AP expression levels at 48 h ($4 \times 10^2 \pm 2 \times 10^2$ versus $4 \times 10^4 \pm 1 \times 10^4$ LU/mg protein, pDNA-NP and pDNANP+LIP, respectively, FIG. 6). A second addition of LIP to the pDNA-NP+LIP group at 48 h resulted in a significant increase of AP expression after 1 week ($4 \times 10^3 \pm 1 \times 10^3$ versus $9 \times 10^4 \pm 1 \times 10^4$ LU/mg protein, respectively). In contrast, the same treatment of the naked pDNA-LIP group resulted in a decrease of AP expression at 1 week ($2 \times 10^7 \pm 1 \times 10^7$ versus $5 \times 10^6 \pm 2 \times 10^6$ LU/mg protein, respectively) A second addition of LIP or pDNA and LIP to the pDNA-LIP group resulted in insignificantly higher AP levels at 1 week ($5 \times 10^6 \pm 2 \times 10^6$ and $5 \times 10^6 \pm 1 \times 10^6$ LU/mg protein, pDNA-LIP and pDNA-LIP+pDNA, respectively). Addition of calcium (which is positively charged dike LIP) to the medium containing pDNA-NP did not result in enhanced transfection efficiency (data not shown). Similarly, no increase in transfection efficiency was found following the addition of the lysosomotropic agent, chloroquine, and the osmotic swelling agent, sucrose (data not shown). The possible deleterious effect of the presence of particles in the cell culture medium on transfection capability of naked pDNA was examined by comparing the expression of cells incubated with pDNA-CaPi to those cells incubated with blank-NP+ pDNA-CaPi (Table 3). The presence of NP, either before (possible pre-transcription effect) or after (possible effect on translation) addition of naked pDNA-CaPi did not affect gene expression levels in comparison to the control group (pDNA-CaPi). These results confirm the suitability of the tested NP formulation for use delivering a foreign gene for expression in various cell types. As stated hereinabove, cationic liposomes such as LIP are subject to inactivation by serum and extracellular matrix components, and often form aggregates. These disadvantages render them unsuitable for use in many in-situ applications, although they are often employed in tissue culture. Further, LIP is not characterized by sustained release, is less amenable to targeting by ligand attachment, and is less biocompatible than NPs of the present invention (see also data presented hereinbelow).

TABLE 3

The possible deleterious effect of the presence of polymeric nanoparticles (NP) in the cell culture on the transfection efficiency in vitro (alkaline phosphatase expression in LU/mg protein after 48 h, 2 µg pDNA, mean ± s.e.m., n = 4

| | 293 endothelial cells | NIH 3T3 Fibroblasts |
|---|---|---|
| CaPi-pDNA | $2.23 \times 10^7 \pm 4.06 \times 10^5$ | $2.23 \times 10^7 \pm 4.06 \times 10^5$ |
| Blank NP before CaPi | $1.29 \times 10^7 \pm 2.57 \times 10^3$ | $1.29 \times 10^7 \pm 2.57 \times 10^3$ |
| Blank NP after CaPi | $3.89 \times 10^7 \pm 1.17 \times 10^7$ | $3.89 \times 10^7 \pm 1.17 \times 10^7$ |

Example 5

Expression of pDNA Delivered in PLGA Nanoparticles In Situ

Expression of an alkaline phosphatase reporter gene in rat tibialis muscle 3, 7 and 28 days after a single i.m. injection of either naked pDNA, pDNA-NP or pDNA-LIP is represented graphically in FIG. 5. Treatment with pDNA-NP resulted in measurable gene expression at all time points. However, AP expression levels were significantly lower at 3 days and comparable at 7 days to those achieved with pDNA treatment ($6.1 \times 10^6 \pm 2.0 \times 10^6$ and $0.2 \times 10^6 \pm 0.05 \times 10^6$ LU/g protein, after 3 days, and $3.9 \times 10^6 \pm 1.2 \times 10^6$ and $1.3 \times 10^6 \pm 0.8 \times 10^6$ LU/g protein, after 7 days, pDNA and pDNA-NP, respectively). It is clinically significant that pDNA-NP mediated AP expression increased between the 3 and 7 day timepoints, while that of naked DNA did not increase ($0.2 \times 10^6 \pm 0.05 \times 10^6$ and $1.3 \times 10^6 \pm 0.8 \times 10^6$ LU/g protein, 3 and 7 days, respectively). After 28 days, pDNA-NP treated animals exhibited significantly higher AP expression levels than naked pDNA treated animals. At all time-points, NP were observed in the injection site (but not in the histological sections). No adverse tissue reaction was observed. Histochemical staining of AP showed that the protein distribution in the tissue was similar for both the pDNA (FIG. 9b), and pDNA-NP groups (FIGS. 8c and d). A similar section from a saline injected animal is presented for comparison (FIG. 9a). These results indicate that the tested nanoparticle formulation is capable of providing sustained expression of a reporter gene in a tissue in the context of a whole animal. Further, the tested nanoparticles do not provoke an unfavorable response from the host as is typically observed with virus mediated delivery systems. Further, the tested nanoparticles are less likely to cause complement activation thal LIP or other cationic liposomes. Further, the tested nanoparticles are more suited to pharmaceutical use because they are easily lyophilized, sterilized and stored for long periods of time.

Example 6

Comparison of Encapsulation of PNA and ODN

The features of PT-ODN and PNA nanoparticles (NP) preparations are summarized in Table 4. Relatively high encapsulation efficiency (amount entrapped) was achieved both for PNA and ODN NPs preparations (68 and 81%, respectively). Addition of calcium chloride to the PVA phase resulted in higher encapsulation of the negatively charged PT-ODN. These results indicate that PNA is less efficiently encapsulated than ODN. However, the tested nanospheres offer a means for intracellular delivery of PNA which has previously been considered infeasible.

TABLE 4

Features of PNA and ODN NPs preparations.

|  | PNA-NP | ODN-NP |
|---|---|---|
| Initial loading (w/w %) | 0.7 | 1.7 |
| Amount in exterior phase (% of initial) | 49.8 ± 8.4 | 18.2 ± 2.1 |
| Amount entrapped (% of initial) | 67.6 ± 1.6 | 81.1 ± 7.2 |
| Final loading (w/w %) | 0.5 | 1.4 |

Mean ± SEM, n = 6.

Example 7

Further Comparison of ODN and PNA Nanoparticles

The sizes of nanoparticles particles formed are summarized in Table 5. All particles formed were in the nano-range (ca. 300 nm). The addition of mannitol before lyophilization resulted in a 100 nm decrease in the final particle size (438±124 and 324±104, with and without mannitol, respectively).

The NPs had a spherical morphology as shown in the TEM micrographs (FIG. 10). No differences were found between blank and loaded NPs.

Figure 11:
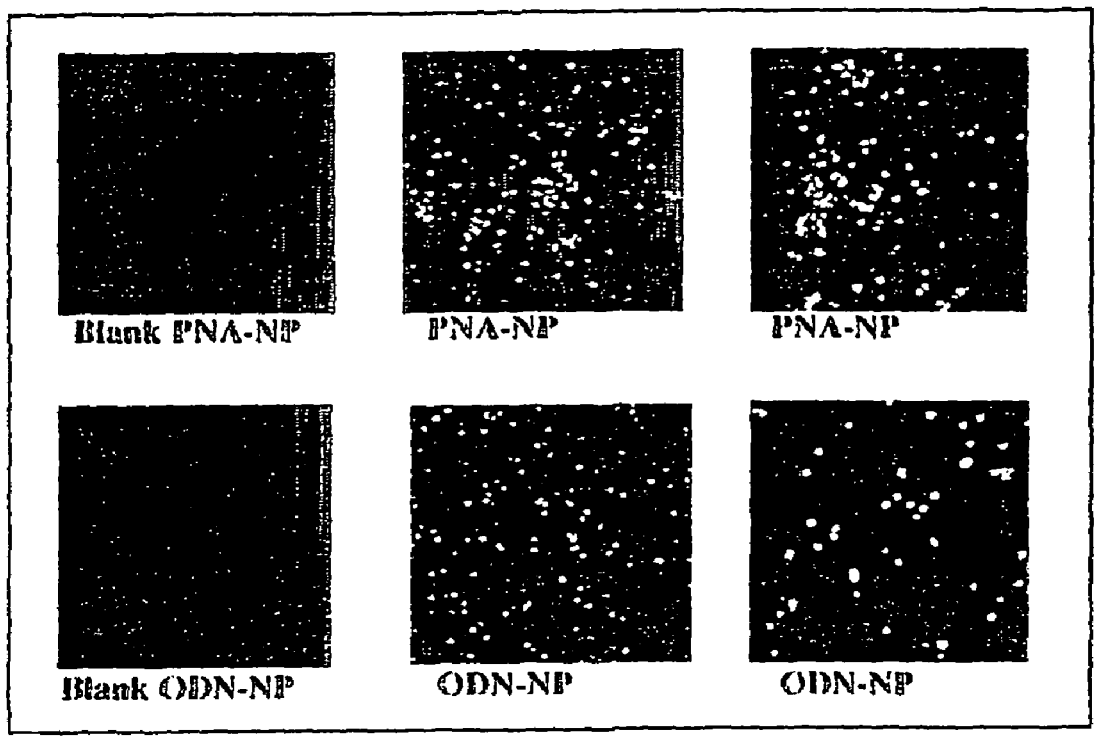
FIG. 11 presents fluorescence micrographs of ODN and PNA loaded NPs. The ODNs and PNA were covalently labeled with FITC prior to encapsulation. Note fluorescence signal in over 90% of the particles. (a) blank PNA-NP; (b+c) PNA-NP; (d) blank ODN-NP; (e+f) ODN-NP.

Labeling of the PT-ODN and the PNA with the fluorescence probe, FITC, showed a fluorescence signal in over 90% of the particles (FIG. 11). These results suggest that despite the differences in loading efficiency presented in table 4, PNA nanoparticles can be prepared. Further, it is important to note that use of antisense sequences (as opposed to plasmid DNA) results in a smaller average particle size (compare to table 1 hereinabove).

TABLE 5

PT-ODN and the PNA NP sizes

|  | Before lyophilization (nm ± SD) | After lyophilization (nm ± SD) |
|---|---|---|
| Blank | 293 ± 81 | 438 ± 124 |
| Blank NPs + 2% mannitol | 291 ± 85 | 324 ± 104 |
| PNA-NPs + 2% mannitol | 287 ± 99 | 301 ± 89 |
| ODN-NPs + 2% mannitol | 279 ± 77 | 301 ± 81 |

Example 8

Relative Release Rates from ODN and PNA Nanoparticles

Figure 12:
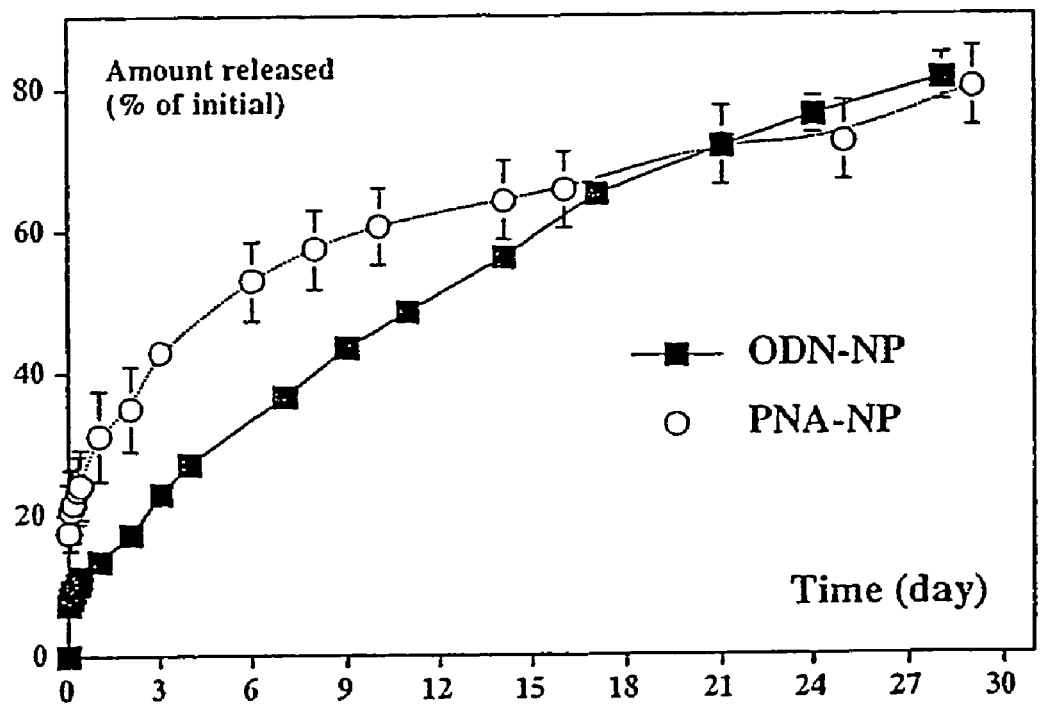
FIG. 12 is a graph illustrating Cumulative release (% of amount encapsulated) as a function of time (days) for ODN and PNA from ODN and PNA-loaded NPs. Release was measured in TE buffer pH 7.4 for ODN or dd sterile water for PNA at 37° C. (mean±SEM, n=4).

In order to determine the suitability of NP as an extended release delivery system for PNA, the relative release rates of ODN and PNA were examined for 30 days. Results are summarized graphically in FIG. 12. Both PT-ODN and PNA were about 80% released over 30 days. Both PT-ODN and PNA were released fastest in the first 3 days (13% PT-ODN and 40% PNA). These results indicate that both ODN and PNA can be delivered over prolonged periods by nanoparticles of the present invention.

Example 9

Comparison of Cellular Incorporation of ODN and PNA Nanoparticles

Figure 13:
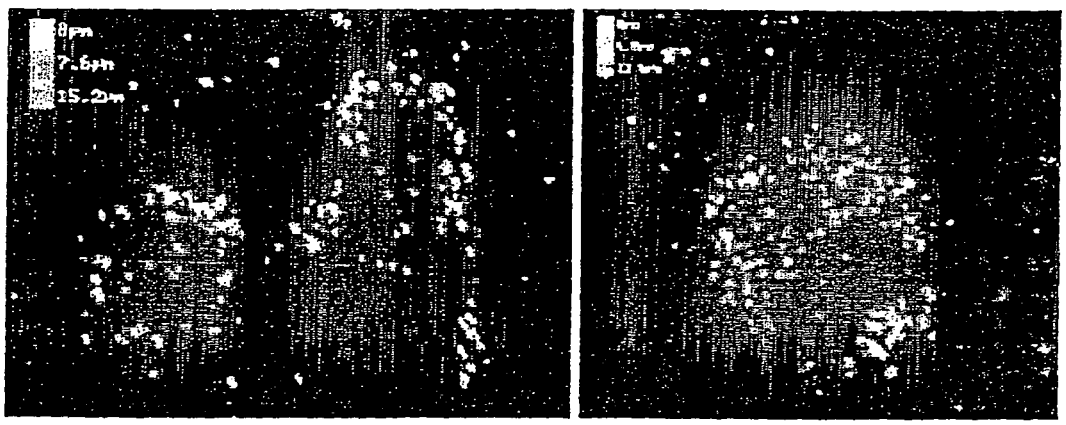
FIG. 13 presents confocal cross-section images of smooth muscle cells 24 hrs. after delivery of fluorescent (FITC)-labeled ODN (a) and PNA (b) encapsulated in NP. Confocal cross-sections verified cell internalization (green color). Note the localization of the NPs in the cytoplasm.

Following the comparison of release rates in Example 8, the ability of PNA nanoparticles to enter cells was compared to that of ODN nanoparticles. Nanoparticles loaded with FITC-labeled ODNs and PNAs were incorporated and accumulated in the cytoplasm of transfected smooth muscle cells SMC (FIG. 13a and b respectively). Blank-NP exhibited very low fluorescence determined as background for further analysis. Naked FITC-labeled ODNs and PNA showed low fluorescence at 2, 5 and 24 hrs. time points (not shown). Confocal cross-section images of SMC 24 hrs. following delivery of fluorescent (FITC)-labeled ODN and PNA encapsulated in NPs are presented in FIGS. 13a and b respectively. Confocal cross-sections verified cell internalization (green color), and cytoplasmic localization of the ODNs. These results, coupled with those of the previous example, indicate that timed release of ODN and/or PNA in living cells may be achieved using nanoparticles according to the present invention.

Example 10

Inhibition of Smooth Muscle Cell Proliferation by Nanoparticles Containing Various ODNs Designed to Block PDGFβR Expression The inhibition of smooth muscle cell (SMC) proliferation following administration of fully PT-ODNs (II-S) in comparison to partially PT-ODNs (II) is summarized in Table 6. ODN antisense sequences to initiation codons were designed to block the translation of the extra cellular domain of rat, mouse and human platelet derived growth factor β-receptor (PDGFβR). The mRNA AUG initiation sites were predicted using an Internet based computer program ATG prediction made available by The Helix Research Institute (HRI; established on Mar. 28, 1996, by the Japan Key Technology Centre; see http://www.hri.co.jp) to identify potential initiation codons in the mRNA sequences of PDGFR-β gene. The AS-ODN sequences were confirmed for both specificity and lack of any secondary structure. Typically, PT-ODNs sequences are 18 bases. Each of the PT-ODNs used had three phosphorothioated linkages at each end. The parallel scrambled (SC) sequences were designed as well. In some cases longer and or fully phosphorothioated sequences were employed.

The specific ODN sequences employed were (* indicates PT linkage):

```
SC (II)     5'-C*G*G*AGAGAGGCCGTCG*A*T*-3'

AS (II)     5'-C*G*G*GAGGAAGCCCATG*G*T*-3'

SC-S        5'-C*G*G*A*G*A*G*A*G*G*C*C*G*T*C*G*A*T*-3'
(II-S)

AS-S        5'-C*G*G*G*A*G*G*A*A*G*C*C*C*A*T*G*G*T*-3'
(II-S)
```

These sequences are herein identified as SEQ. ID. NOs. 1-4 respectively. These sequences were chosen because they are antisense analogs to sequence around the ATG at 77 (complementary to aa 74-85).

No difference was found in inhibition between antisense (AS) and scrambled (SC) sequences at 10 μM regardless of level of PT modification of the ODNs (Table 6). At 5 μM, application of naked partially PT-ODNs AS resulted in 3.5 times higher inhibition than that obtained with the SC sequence (29.62□9.80 versus 8.55□7.22% for AS (II) and SC (II), respectively). Moreover, there was no difference between AS and SC effects following application of the fully PT-ODN at this concentration (28.22□3.43 versus 24.02 ϵ 1.46% for AS-S (II-S) and SC-S (II-S), respectively).

Figure 14:
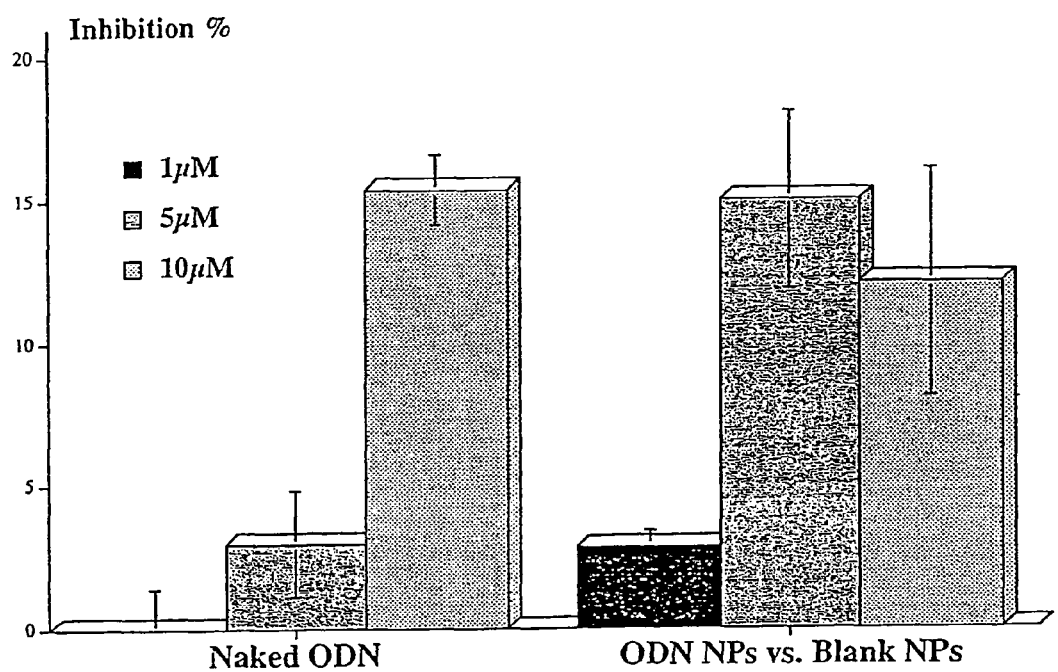
FIG. 14 is a bar graph illustrating % Inhibition of SMC proliferation by ODN-NPs. The effect of ODN-NPs was compared to the parallel naked sequences at concentrations of 1, 5 and 10 μM. The results are presented as antisense (AS-III) minus scrambled (SC-III) effects and also as loaded NPs (AS, SC) minus blank NPs effects, in order to examine the effect of blank NPs. (Inhibition %, 3 days, mean □SD, n=3, differences between the groups were not statistically significant).

The results of SMC inhibition following treatment with naked R-AS-PT-ODN (III) (5'-T*A*T*CACTCCTGGAAGC*C*C*-3'; SEQ. ID. No. 5) or naked R-SC-PT-ODN (III) (5'-T*T*A*CACTCCTGGACAG*C*C*-3'; SEQ. ID. No. 6), and nanoparticles containing the same molecules are summarized graphically in FIG. 14. These sequences are similar to those employed in previous research as fully phosphorothioated sequences (Sirois et al. (1997) Circulation. 95:669-676). Inhibition induced by each naked sequence was determined by comparison to the control group (i.e. cells only) which was termed 100% (see materials and methods). Inhibitory % of ODN-NPs was determined by comparison to blank NPs. The scrambled sequence (SC) showed an inhibitory effect as well, but to a lesser extent than the antisense (AS) sequence. Therefore, the results are presented as antisense effect minus the scrambled effect (both for naked and encapsulated). Blank NPs failed to demonstrate an inhibitory effect, and the cell number was similar to the cell only control group (data not shown). Dose response antiproliferative effect was found for naked ODNs at concentrations of 1 to 10 μM and for ODNs-NP at concentrations of 1 and 5 μM. PT-ODN NPs were more potent than naked PT-ODN in inhibiting SMCs at low concentrations of 1 and 5 μM (0.3☐51.8 and 3.0☐1.9 versus 2.6☐0.5 and 15.5☐3.2%, naked ODN-NPs versus ODN-NPs for 1 and 5 μM, respectively). No difference was found at a concentration of 10 μM between naked ODN and encapsulated ODN in inhibiting SMC proliferation. Moreover, following ODN-NPs delivery the inhibition effect at 10 μM did not increase in comparison to the effect observed at 5 μM. These results indicate that encapsulation of partially phosphorothioated ODNs in nanoparticles can allow a low concentration (relative to the same sequence delivered as naked DNA) of ODN to act specifically and in a dose dependent fashion.

TABLE 6

Inhibition of SMC proliferation following naked antisense oligonucleotides administration. The effect of the partially phosphorothioated sequences SC/AS (II), was compared to the parallel fully phosphorothioated sequences SC/AS (II-S) at concentrations of 5 and 10 ☐M. Percent inhibition was calculated as [1 − (average cell number in treated wells/average cell number in control wells)] * 100. Inhibition % at 3 days, mean ☐ SEM, n = 3, differences between the groups were not statistically significant.

| SEQUENCE | Inhibition % 5 μM | 10 μM |
|---|---|---|
| SC (II) | 8.55 ± 7.22 | 34.73 ± 3.34 |
| AS (II) | 29.62 ± 9.80 | 27.06 ± 1.40 |
| SC-S (II-S) | 24.02 ± 1.46 | 36.44 ± 8.66 |
| AS-S (II-S) | 28.22 ± 3.43 | 43.99 ± 12.55 |

Example 11

Inhibition of Proliferation of ZnR5 Cells which Express Human PDGFβR

In order to assess the efficacy of the ODN sequences described hereinabove in an additional cellular system, inhibition of ZnR5 cell proliferation following treatment with naked human AS sequences (SEQ. ID. NOs. 7 and 9) was measured. Results are summarized graphically in figures in FIGS. 15a and b.

Figure 15A:
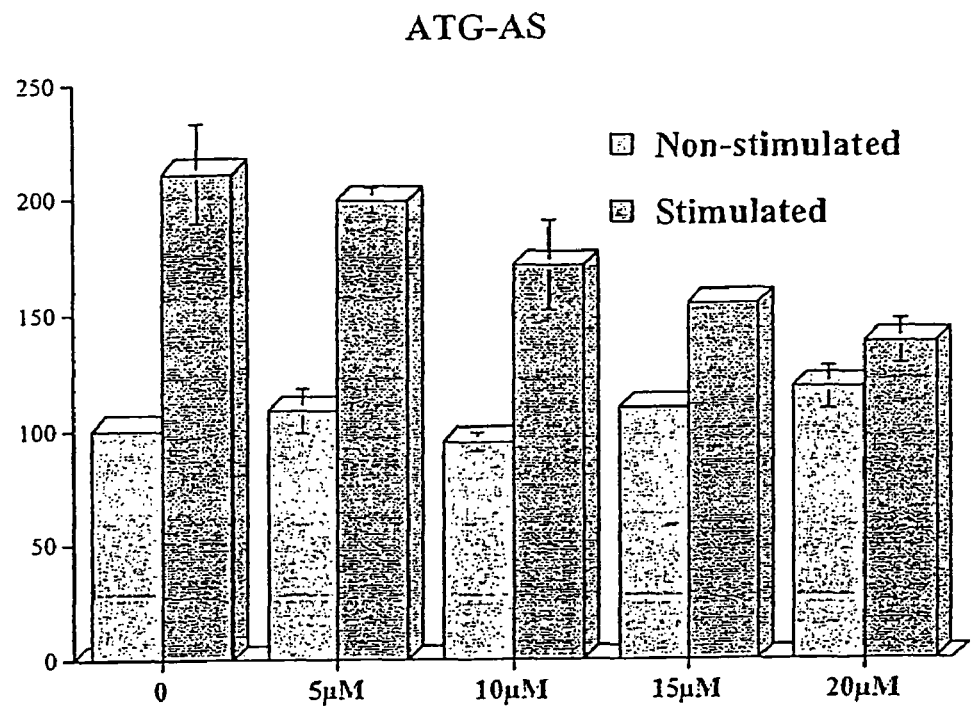
FIGS. 15a and 15b are bar graphs illustrating Inhibition of ZnR5 proliferation by naked human PDGFRb sequences. The effect of AS was studied at concentrations of 5 to 20 μM. The results following transfection with the ATG sequence are presented in (a) the results following transfection with the UTR sequence are presented in (b). The ATG AS was designed against the 5'-357 region and the 5'-UTR was designed against the 21-39 region (see materials and methods for details). Inhibition %, 3 days, mean□SD, n=3.

Following administration of ATG sequences (SEQ. ID. NOs. 7 and 8; antisense and scrambled negative control respectively; FIG. 15A) no significant inhibition of proliferation was observed in non-stimulated ZnR5 cells. In stimulated ZnR5 cells, inhibition was observed only at high concentrations (in excess of 10 μm). The observed inhibition was dose dependent.

Figure 15B:
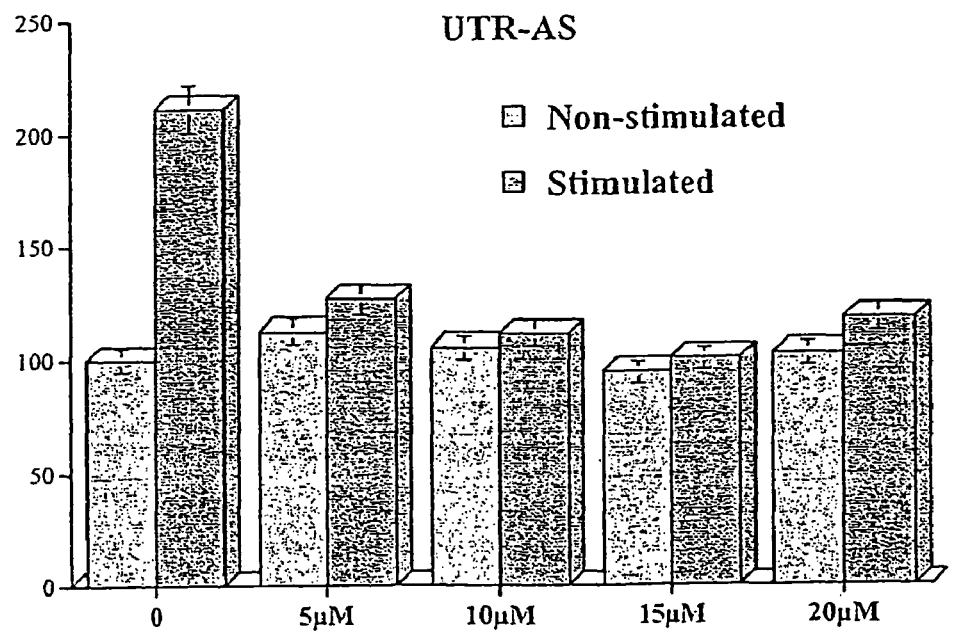

Administration of UTR sequences (SEQ. ID. NOs. 9 and 10 antisense and scrambled negative control respectively; FIG. 15B) caused no significant inhibition of proliferation in non-stimulated ZnR5 cells. In contrast to results employing SEQ. ID. NO. 7, significant inhibition was observed at concentrations as low as 5 μM. However, the inhibition was not dose dependent in the tested range of concentrations, perhaps indicating saturation of the inhibition effect.

Scrambled sequences (SEQ. ID. NOs. 8 and 10) were found inactive in all experiments employing ZnR5 cells.

These results demonstrate that the UTR sequences are more efficient for inhibition of transcription.

Example 12

Figure 16B:
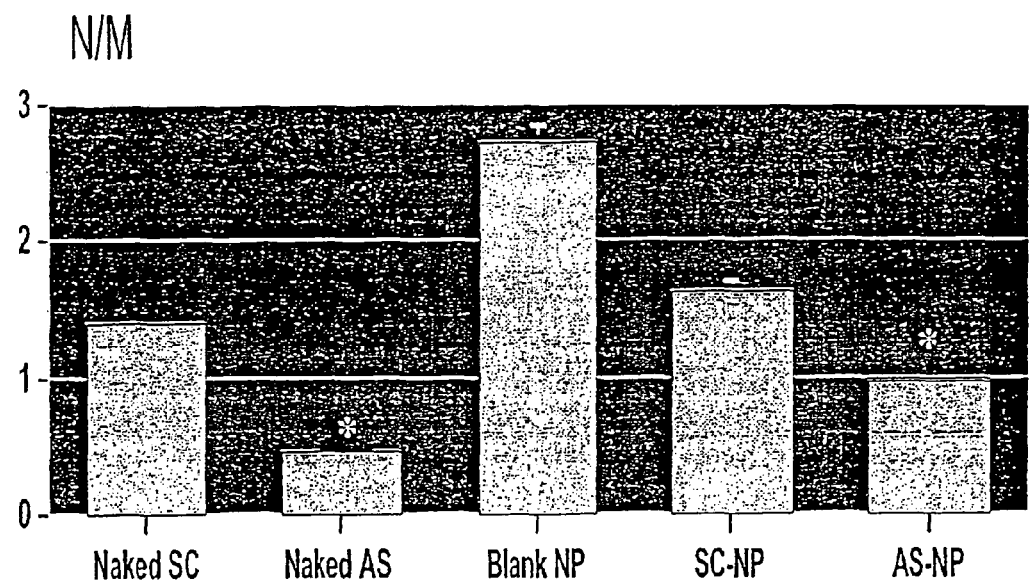
FIGS. 16a, and 16b are bar graphs illustrating inhibition of neointimal formation 14 days after balloon injury to rat carotid artery by intraluminal instillations of 20 □M/50 □l (1 nmole) of naked AS/SC PT-ODN and comparable amounts of AS/SC NP suspension (SEQ. ID. NOs 2 and 1 respectively, see M&M). Stenosis % and n/m are shown (panels a and b respectively). Mean□SEM, mean was calculated from the maximal degree of neointimal formation slide section of each artery. For naked sequences, *p<0.05 in comparison to the SC sequence. For NPs, *p<0.05 in comparison to SC-NP and blank NP.
Figure 16A:
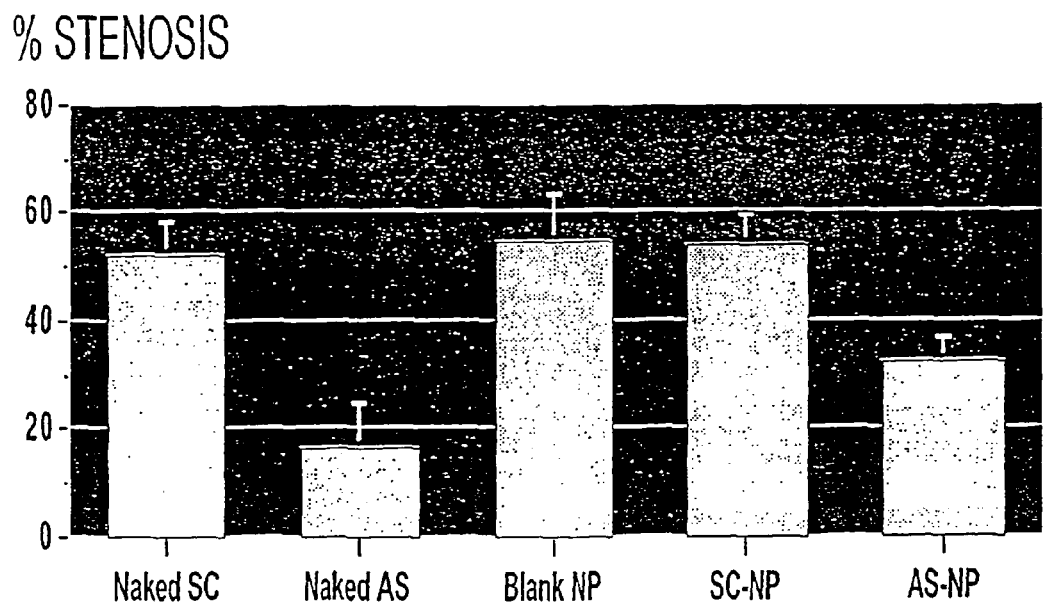
Figure 16C:
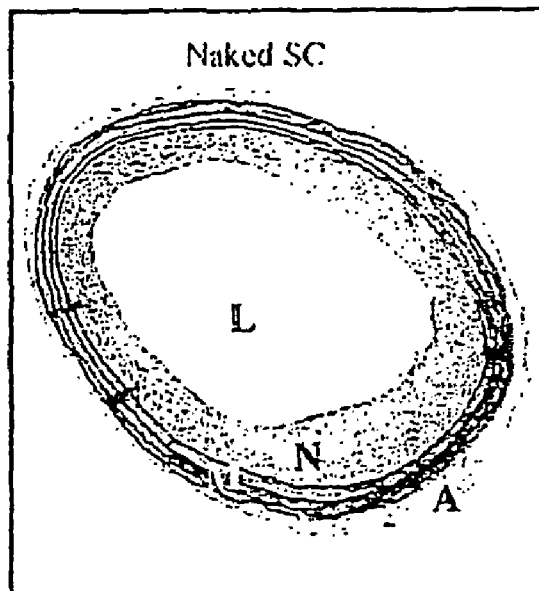
FIGS. 16c, 16d, 16e, 16f, 16g, 16h, 16i, 16j, 16k and 16l are photomicrograpghs illustrating inhibition of neointimal formation 14 days after balloon injury to rat carotid artery by intraluminal instillations of 20 μM/50 μl (1 nmole) of naked AS/SC PT-ODN (16c, 16d, 16e, 16f) and similar amounts of AS/SC NP suspensions (16g, 16h, 16i, 16j, 16k and 16l). Photomicrographs of representative histological sections are shown. Verhoeff's elastin stain, magnification ×(c, d, g, h and i) and magnification ×12.5 (e, f, j, k and 1). L=lumen; N=neointima; M=media; and A=adventitia).
Figure 16D:
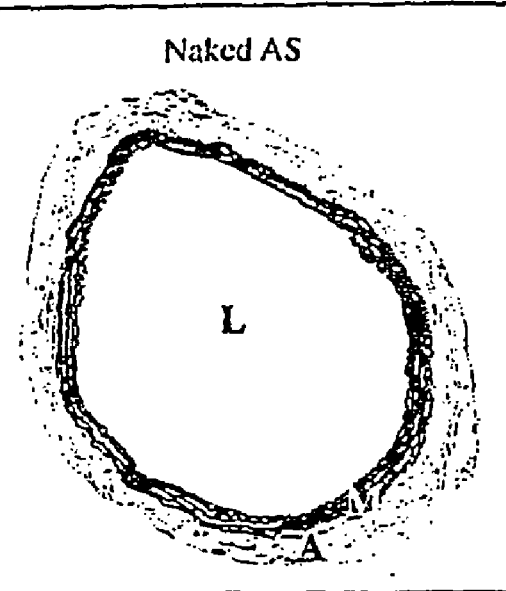
Figure 16E:
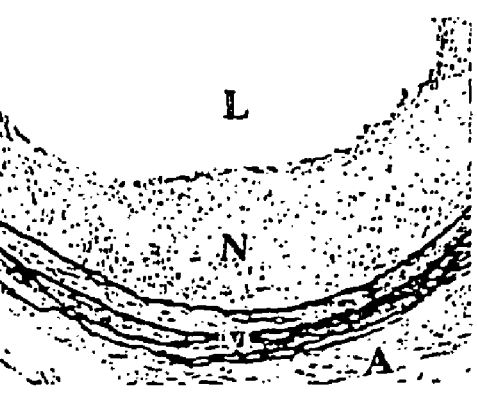
Figure 16F:
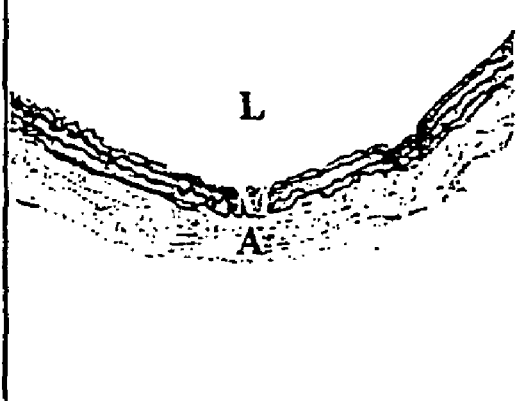
Figure 16G:
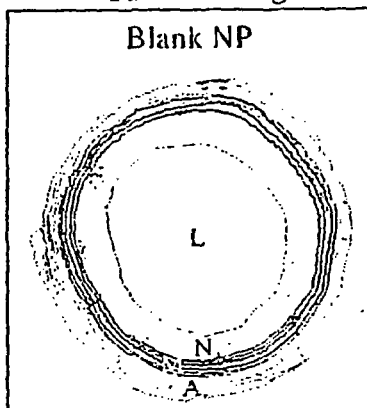
Figure 16H:
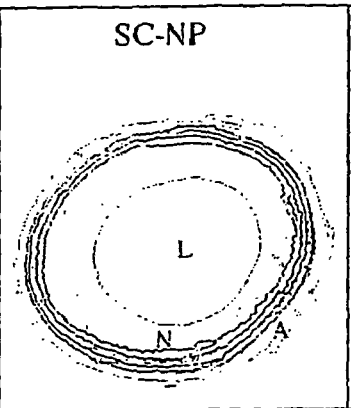
Figure 16I:
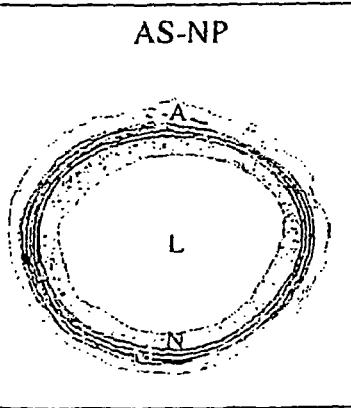
Figure 16J:
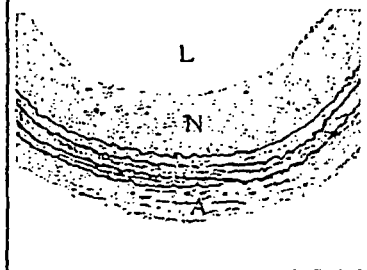
Figure 16K:
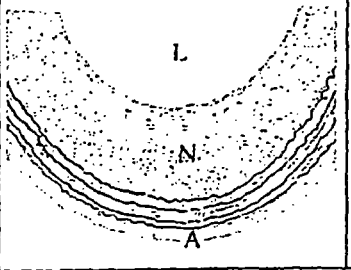
Figure 16L:
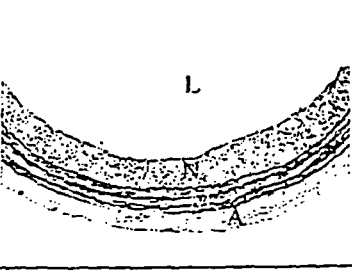

Inhibition of Neointimal Formation Using PDGFβR Antisense Nucleic Acid Homologs in a Rat Injured Carotid Model In order to determine the suitability of nanoparticle encapsulated ODNs in a clinical model, the extent of mean neointimal formation was measured in a Rat injured carotid model as described hereinabove in methods and materials. Mean neointimal formation was determined 14 days after injection of AS-NP containing PDGFβR sequences (SEQ. ID. NOs 2 and 1; antisense and scrambled negative control respectively). Results, expressed as a percent of luminal stenosis, were 32.21±4.75% in comparison to 54.89±8.84 and 53.84±5.58% in the blank-NP and SC-NP groups, respectively ($p<0.05$, table 7 and FIGS. 16a). Similarly, statistically significant reductions of the mean neointima-to-media ratio were found in the ASF-NP treated group in comparison to the blank-NP and SC-NP groups (0.96±0.16 versus 2.01±0.43 and 1.63±0.21, respectively, $p<0.05$, Table 7 and FIG. 16b).

Treatment with naked AS resulted in inhibition of neointima formation by 3.1 fold in comparison to naked SC treatment (16.76±7.97 compared with 51.85±6.77% stenosis. respectively, $p<0.05$). Similarly, significant reductions of the mean neointima-to-media ratio were found in the naked AS treated group in comparison to the naked SC group (0.46±0.27 versus 1.4±0.17, respectively, $p<0.05$, Table 7 and FIGS. 16a and b).

The reduction of both % stenosis and N/M ratio was 3.1 fold in the naked AS treated group and 1.7 fold in the AS-NP treated group, but the differences between the two groups were not statistically significant.

TABLE 7

Inhibition of neointimal formation 14 days after balloon injury to rat carotid artery by intraluminal instillations of 20 μM/50 μl (1 nmole) of naked AS/SC PT-ODN (sequence II, see M&M) and comparable amounts of AS/SC NP suspension.

| | MEDIA | % STENOSIS | N/M |
|---|---|---|---|
| Naked SC (n = 5) | 0.11 ± 0.01 | 51.85 ± 6.77 | 1.40 ± 0.17 |
| Naked AS (n = 8) | 0.11 ± 0.02 | 16.76 ± 7.97 * | 0.46 ± 0.27 * |
| Blank NP (n = 7) | 0.11 ± 0.01 | 54.89 ± 8.84 | 2.7 ± 0.43 |
| SC-NP (n = 7) | 0.12 ± 0.01 | 53.84 ± 5.58 | 1.63 ± 0.21 |
| AS-NP (n = 7) | 0.10 ± 0.01 | 32.21 ± 4.75 * | 0.96 ± 0.16 * |

Mean ± SEM, mean was calculated from the maximal degree of neointimal formation slide section of each artery. For naked sequences, * $p < 0.05$ in comparison to the SC sequence. For NPs, * $p < 0.05$ in comparison to SC-NP and blank NP.

Medial areas were found similar in all groups (p>0.5, Table 7). Morphometric results obtained by the morphometric analysis of all sections in the slide correlated very well with the data presented above based on averages of the most constricted sections.

Photomicrographs of representative histological sections are shown in FIGS. 16c-l. The reduction in neointima (N) formation following treatment with the naked AS sequence (FIGS. 16c-f) and AS-NP (FIGS. 16g-l) in comparison to the control groups is apparent.

These results clearly indicate that nanosphere encapsulated ODNs according to the present invention may be advantageously employed in conteracting restenosis after balloon angioplasty. Further, the absence of immune or tumorigenic response in the sections presented suggests that the nanospheres of the present invention are amenable to use in a wide range of clinical applications.

The present invention has the potential to provide transgenic gene and polymorphic gene animal and cellular (cell lines) models as well as for knockout models. These models may be constructed using standard methods known in the art and as set forth in U.S. Pat. Nos. 5,487,992, 5,464,764, 5,387,742, 5,360,735, 5,347,075, 5,298,422, 5,288,846, 5,221,778, 5,175,385, 5,175,384, 5,175,383, 4,736,866 as well as Burke and Olson, Methods in Enzymology, 194:251-270 1991); Capecchi, Science 244:1288-1292 1989); Davies et al., Nucleic Acids Research, 20 (11) 2693-2698 1992); Dickinson et al., Human Molecular Genetics, 2(8): 1299-1302 1993); Duff and Lincoln, "Insertion of a pathogenic mutation into a yeast artificial chromosome containing the human APP gene and expression in ES cells", Research Advances in Alzheimer's Disease and Related Disorders, 1995; Huxley et al., Genomics, 9:742-750 1991); Jalcobovits et al., Nature, 362:255-261 1993); Lamb et al., Nature Genetics, 5: 22-29 1993); Pearson and Choi, Proc. Natl. Acad. Sci. USA 1993). 90:10578-82; Rothstein, Methods in Enzymology, 194:281-301 1991); Schedl et al., Nature, 362: 258-261 1993); Strauss et al., Science, 259:1904-1907 1993). Further, patent applications WO 94/23049, WO93/14200, WO 94/06908, WO 94/28123 also provide information.

All such transgenic gene and polymorphic gene animal and cellular (cell lines) models and knockout models for restenosis, cancer, other cell proliferation disorders, other genetic defects or therapy thereof, derived from claimed embodiments of the present invention, constitute preferred embodiments of the present invention.

Gene therapy as used herein refers to the transfer of genetic material (e.g. DNA, RNA, PNA or derivatives thereof) of interest into a host to treat or prevent a genetic or acquired disease or condition or phenotype. The genetic material of interest encodes a product (e.g. a protein, polypeptide, peptide, functional RNA, antisense, ribozyme) whose production in vivo is desired. For example, the genetic material of interest can encode a hormone, receptor, enzyme, polypeptide or peptide of therapeutic value. For review see, in general, the text "Gene Therapy" (Advances in Pharmacology 40, Academic Press, 1997).

Two basic approaches to gene therapy have evolved: (1) ex vivo and (2) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ.

In in vivo gene therapy, target cells are not removed from the subject rather the genetic material to be transferred is introduced into the cells of the recipient organism in situ, that is within the recipient. In an alternative embodiment, if the host gene is defective, the gene is repaired in situ (Culver, 1998. (Abstract) Antisense DNA & RNA based therapeutics, February 1998, Coronado, Calif.).

These genetically altered cells have been shown to express the transfected genetic material in situ.

The gene expression vehicle is capable of delivery/transfer of heterologous nucleic acid into a host cell. The expression vehicle may include elements to control targeting, expression and transcription of the nucleic acid in a cell selective manner as is known in the art. It should be noted that often the 5'-UTR and/or 3'-UTR of the gene may be replaced by the 5'-UTR and/or 3'-UTR of the expression vehicle. Therefore, as used herein the expression vehicle may, as needed, not include the 5'-UTR and/or 3'-UTR of the actual gene to be transferred and only include the specific amino acid coding region.

The expression vehicle can include a promoter for controlling transcription of the heterologous material and can be either a constitutive or inducible promoter to allow selective transcription. Enhancers that may be required to obtain necessary transcription levels can optionally be included. Enhancers are generally any nontranslated DNA sequence which works contiguously with the coding sequence (in cis) to change the basal transcription level dictated by the promoter. The expression vehicle can also include a selection gene as described herein below.

Vectors can be introduced into cells or tissues by any one of a variety of known methods within the art. Such methods can be found generally described in Sambrook et al., Molecular Cloning: A Laboratory Manual, Cold Springs Harbor Laboratory, New York 1989, 1992), in Ausubel et al., Current Protocols in Molecular Biology, John Wiley and Sons, Baltimore, Md. 1989), Chang et al., Somatic Gene Therapy, CRC Press, Ann Arbor, Mich. 1995), Vega et al., Gene Targeting, CRC Press, Ann Arbor Mich. (995), Vectors: A Survey of Molecular Cloning Vectors and Their Uses, Butterworths, Boston Mass. 1988) and Gilboa et al. (Biotechniques 4 (6): 504-512, 1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. Nanoparticles comprising:
   (a) a biodegradable polymer PLGA [poly(DL-lactide-co-glycolide)] of a lactide:glycolide ratio of 50:50 in combination with a cationic or neutral liposomal formulation comprising DOSPA or a 1:1 ratio of DOTAP:DOPE;
   (b) an isolated, bioactive nucleic acid sequence encapsulated within the PLGA, wherein said nanoparticles are capable of releasing said isolated, bioactive nucleic acid sequence over an extended period of time; and
   (c) the amino acid-sequence as set forth in SEQ ID NO:25.

2. The nanoparticles of claim 1, wherein said nanoparticles further comprise a salt of a divalent cation.

3. The nanoparticles of claim 2, wherein said divalent cation is calcium.

4. The nanoparticles of claim 1, wherein the amino acid sequence is operative to impart to said nanoparticles a specific affinity for at least one target selected from the group consisting of an LDL receptor and a GAG-binding region of apoB-100.

5. The nanoparticles of claim 1, further including mannitol.

* * * * *